US010779747B2

(12) United States Patent
Simon

(10) Patent No.: US 10,779,747 B2
(45) Date of Patent: *Sep. 22, 2020

(54) SYSTEM AND SIGNATURES FOR THE MULTI-MODAL PHYSIOLOGICAL STIMULATION AND ASSESSMENT OF BRAIN HEALTH

(71) Applicant: Cerora, Inc., Bethlehem, PA (US)

(72) Inventor: Adam J. Simon, Yardley, PA (US)

(73) Assignee: Cerora, Inc., Yardley, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/773,878

(22) PCT Filed: Mar. 14, 2014

(86) PCT No.: PCT/US2014/028061
§ 371 (c)(1),
(2) Date: Sep. 9, 2015

(87) PCT Pub. No.: WO2014/143896
PCT Pub. Date: Sep. 18, 2014

(65) Prior Publication Data
US 2016/0022167 A1    Jan. 28, 2016

Related U.S. Application Data

(60) Provisional application No. 61/799,842, filed on Mar. 15, 2013, provisional application No. 61/836,294, (Continued)

(51) Int. Cl.
*A61B 5/0484*    (2006.01)
*A61B 5/16*    (2006.01)
(Continued)

(52) U.S. Cl.
CPC ...... *A61B 5/04842* (2013.01); *A61B 5/02405* (2013.01); *A61B 5/0478* (2013.01);
(Continued)

(58) Field of Classification Search
CPC ......... A61B 4/0476; A61B 5/024; A61B 5/02; A61B 5/16; A61B 5/04842; A61B 5/163;
(Continued)

(56) References Cited

U.S. PATENT DOCUMENTS 3,910,258 A    10/1975   Pisarski et al.
4,988,183 A    1/1991    Kasahara et al.
(Continued)

FOREIGN PATENT DOCUMENTS

AU    2014240105 A1    11/2015
CA    2904264 A1    9/2014
(Continued)

OTHER PUBLICATIONS

Michael McCrea, Standardized Mental Status Testing on the Sideline After Sport-Related Concussion, 2001, Journal of Athletic Training, 36(3), 274-279.*
(Continued)

*Primary Examiner* — Christopher Koharski
*Assistant Examiner* — James Moss
(74) *Attorney, Agent, or Firm* — Schwegman Lundberg & Woessner, P.A.

(57) ABSTRACT

A system for assessing brain health of a user includes an electronics module including an active brainwave sensor that collects channels of electroencephalography (EEG) brainwave data, a plurality of biological sensors, and a stimulation device. The biological sensors include a microphone that captures verbal responses of the subject during a battery of tasks, an image sensor that records eye positions, eye saccade and other biometric identification information,
(Continued)

an accelerometer, a gyrometer, a thermometer, a pulse oximetry sensor, a dermal skin conductance sensor, and key strokes, mouse clicks or touch events to measure cognitive data of the user. The stimulation device applies a battery of tasks including a visual or photic stimulant, an auditory stimulant, a gastronomic stimulant, an olfactory stimulant, a touch stimulant, and a cognitive challenge stimulant to the user. The plurality of biological sensors simultaneously measure the body's response to stimulants for recordation by the electronics module.

13 Claims, 24 Drawing Sheets

Related U.S. Application Data filed on Jun. 18, 2013, provisional application No. 61/932,915, filed on Jan. 29, 2014.

(51) Int. Cl.
*A61B 5/145* (2006.01)
*A61B 5/00* (2006.01)
*A61B 5/024* (2006.01)
*A61B 5/0478* (2006.01)
*A61B 5/053* (2006.01)
*A61B 5/11* (2006.01)

(52) U.S. Cl.
CPC ...... *A61B 5/04845* (2013.01); *A61B 5/04847* (2013.01); *A61B 5/0533* (2013.01); *A61B 5/14542* (2013.01); *A61B 5/163* (2017.08); *A61B 5/4064* (2013.01); *A61B 5/4088* (2013.01); *A61B 5/6803* (2013.01); *A61B 5/024* (2013.01); *A61B 5/1118* (2013.01)

(58) Field of Classification Search
CPC . A61B 5/4088; A61B 5/6803; A61B 5/04847; A61B 5/0533; A61B 5/0478; A61B 5/02405; A61B 5/4064; A61B 5/14542; A61B 5/04845; A61B 5/1118
See application file for complete search history.

(56) References Cited

U.S. PATENT DOCUMENTS

| | | | |
|---|---|---|---|
| 6,381,481 B1 | 4/2002 | Levendowski et al. | |
| 6,434,419 B1 | 8/2002 | Gevins et al. | |
| 6,527,730 B2 | 3/2003 | Blazey et al. | |
| 6,741,888 B2 | 5/2004 | Musha et al. | |
| 6,947,790 B2 | 9/2005 | Gevins et al. | |
| 2002/0052311 A1 | 5/2002 | Solomon et al. | |
| 2003/0060499 A1 | 3/2003 | Tulloch | |
| 2003/0181821 A1 | 9/2003 | Greenwald et al. | |
| 2003/0187490 A1* | 10/2003 | Gliner ................. | A61N 1/0531 607/116 |
| 2004/0059241 A1 | 3/2004 | Suffin | |
| 2006/0129324 A1 | 6/2006 | Rabinoff et al. | |
| 2008/0208073 A1 | 8/2008 | Causevic | |
| 2009/0018407 A1 | 1/2009 | Jung et al. | |
| 2009/0018419 A1* | 1/2009 | Torch ..................... | A61B 3/112 600/318 |
| 2009/0036799 A1 | 2/2009 | Sandhu et al. | |
| 2009/0306741 A1* | 12/2009 | Hogle ................. | A61N 1/36082 607/54 |
| 2010/0016751 A1 | 1/2010 | Hunter et al. | |
| 2010/0042011 A1 | 2/2010 | Doidge et al. | |
| 2010/0113960 A1 | 5/2010 | Scheib | |
| 2010/0143256 A1 | 6/2010 | Suffin et al. | |
| 2010/0286532 A1 | 11/2010 | Farringdon et al. | |
| 2010/0312105 A1 | 12/2010 | Hurtt | |
| 2011/0015503 A1 | 1/2011 | Joffe et al. | |
| 2011/0046473 A1* | 2/2011 | Pradeep ............... | A61B 5/0484 600/413 |
| 2012/0150545 A1* | 6/2012 | Simon .................. | A61B 5/0476 704/270 |
| 2012/0251989 A1 | 10/2012 | Wetmore et al. | |
| 2013/0035579 A1 | 2/2013 | Le et al. | |
| 2013/0096405 A1* | 4/2013 | Garfio ................ | A61B 5/14552 600/340 |
| 2014/0114165 A1* | 4/2014 | Walker ............... | A61B 5/04005 600/383 |
| 2015/0313496 A1* | 11/2015 | Connor ................ | A61B 5/0476 600/301 |
| 2015/0324692 A1* | 11/2015 | Ritchey .................. | G16H 40/63 348/14.08 |
| 2016/0015289 A1* | 1/2016 | Simon ................ | A61B 5/04842 600/301 |
| 2016/0022206 A1 | 1/2016 | Simon et al. | |

FOREIGN PATENT DOCUMENTS

| | | | | |
|---|---|---|---|---|
| CN | 101322045 A | 12/2008 | | |
| CN | 101371261 A | 2/2009 | | |
| CN | 101427915 A | 5/2009 | | |
| CN | 102014742 | 4/2011 | | |
| CN | 102686145 A | 9/2012 | | |
| CN | 105592798 A | 5/2016 | | |
| CN | 105658134 A | 6/2016 | | |
| CN | ZL201480028481.5 | 11/2019 | | |
| EP | 0204459 A2 * | 12/1986 | ......... | A61B 5/02427 |
| EP | 2967354 A1 | 1/2016 | | |
| JP | 2016517325 A | 6/2016 | | |
| JP | 2016521998 A | 7/2016 | | |
| KR | 1020160055103 A | 5/2016 | | |
| KR | 1020160138339 A | 12/2016 | | |
| WO | WO 2005/120339 A1 | 12/2005 | | |
| WO | WO-2010147913 A1 * | 12/2010 | .......... | A61B 5/0476 |
| WO | WO-2012106593 A2 | 8/2012 | | |
| WO | WO-2012135654 A1 | 10/2012 | | |
| WO | WO-2013012739 A1 | 1/2013 | | |
| WO | WO-2014143896 A2 | 9/2014 | | |
| WO | WO-2014143896 A3 | 9/2014 | | |
| WO | WO 2014152110 A1 | 9/2014 | | |

OTHER PUBLICATIONS

David R. Bell, Systematic Review of the Balance Error Scoring System, May 2011, Sports Health, 3(3), 287-295.*
Robert Graham, Sports-Related Concussions in Youth, Improving the science, Changing the Culture, 2014, National Academy of Sciences.*
David Bell, et al. "Systematic review of the balance error scoring system." Sports health vol. 3,3 (2011): 287-95. doi:10.1177/1941738111403122, https://www.ncbi.nlm.nih.gov/pmc/articles/PMC3445164/, viewed on Aug. 2, 2019.*
Michael McCrea, "Standardized Mental Status Testing on the Sideline After Sport-Related Concussion.", Journal of athletic training vol. 36,3 (2001): 274-279, https://www.ncbi.nlm.nih.gov/pmc/articles/PMC155418/, viewed on Aug. 2, 2019.*
Scott Piland et al., "Structural Validity of a Self-Report Concussion-Related Symptom Scale", Medicine & Science in Sports & Exercise: Jan. 2006—vol. 38—Issue 1—p. 27-32, viewed on Aug. 2, 2019.*
"SCAT2 Sport Concussion Assessment Tool 2", SCA Tool, http://www.cces.ca/files/pdf/SCAT2%5B1%5D.pdf, 2001, accessed Jun. 3, 2014, 4 pages.
Bell et al., "Systematic Review of the Balance Error Scoring System", Sports Health, 2011, vol. 3, No. 3, 287-295.
"Chinese Application Serial No. 201480027238.1, Response filed May 7, 2018 to Office Action dated Jan. 4, 2018", W English Translation, 8 pgs.
"European Application Serial No. 14762521.4, Response filed Aug. 24, 2018 to Communication Pursuant to Article 94(3) EPC dated Feb. 16, 2018", 11 pgs.
"Australian Application Serial No. 2014228116, First Examination Report dated Jan. 12, 2018", 3 pgs.

(56) References Cited

OTHER PUBLICATIONS

"Chinese Application Serial No. 201480027238.1, Office Action dated Sep. 19, 2018", w English Translation, 22 pgs.
"Chinese Application Serial No. 201480027238.1, Office Action dated Jan. 4, 2018", 21 pgs.
"European Application Serial No. 14762521.4, Communication Pursuant to Article 94(3) EPC dated Feb. 16, 2018", 5 pgs.
"European Application Serial No. 14762521.4, Extended European Search Report dated Oct. 7, 2016", 7 pgs.
"European Application Serial No. 14762521.4, Response filed May 4, 2017 to Extended European Search Report dated Oct. 7, 2016", 9 pgs.
"International Application Serial No. PCT/US2014/028061, International Preliminary Report on Patentability dated Sep. 24, 2015", 7 pgs.
"International Application Serial No. PCT/US2014/028061, International Search Report dated Aug. 28, 2014", 4 pgs.
"International Application Serial No. PCT/US2014/028061, Written Opinion dated Aug. 28, 2014", 5 pgs.
"SCA Tool SCAT2'", Accessed from the internet: Jun. 3, 2014 from URL: <http://www.cces.ca/files/pdfs/SCAT2%5B1%5D.pdf>, (2001), p. 2, Box 5; p. 3, box 8.
"Screen Shot confirming publication date of SCA Tool SCAT2'", Screen image made Jun. 3, 2014 from Google search; URL: <https://www.google.com/search?q=scat2&oq=scat2&aqs=chrome.0.69i59j69i6013j69i57j69i59.1875j0j4&sourceid=chrome&es_sm=122&ie=UTF-8#q=scat2>.
Robert, M Herndon, "Neurologic Rating Scales (second edition of the original version)", (Jan. 31, 2010), 320-321.
Zhang, Sai, et al., "Modern Neurotrauma and Neurosurgery Disease", (Nov. 30, 2010), 128-129.
"U.S. Appl. No. 14/773,872, Final Office Action dated Nov. 2, 2018", 28 pgs.
"U.S. Appl. No. 14/773,872, Non Final Office Action dated Mar. 28, 2018", 21 pgs.
"U.S. Appl. No. 14/773,872, Non Final Office Action dated Dec. 31, 2019", 29 pgs.
"U.S. Appl. No. 14/773,872, Preliminary Amendment filed Sep. 9, 2015", 3 pgs.
"U.S. Appl. No. 14/773,872, Response filed May 2, 2019 to Final Office Action dated Nov. 2, 2018", 28 pgs.
"U.S. Appl. No. 14/773,872, Response filed Jun. 28, 2018 to Non Final Office Action dated Mar. 28, 2018", 17 pgs.
"Australian Application Serial No. 2014240105, First Examination Report dated Oct. 7, 2018", 7 pgs.
"Australian Application Serial No. 2014240105, Subsequent Examiners Report dated Sep. 24, 2019", 5 pgs.
"Chinese Application Serial No. 201480027238.1, Office Action dated Apr. 12, 2019", w/English Translation, 18 pgs.
"Chinese Application Serial No. 201480027238.1, Office Action dated Sep. 26, 2019", W/English Translation, 19 pgs.
"Chinese Application Serial No. 201480027238.1, Response filed Jun. 19, 2019 to Office Action dated Apr. 12, 2019", w/English Claims, 14 pgs.
"Chinese Application Serial No. 201480027238.1, Response filed Dec. 4, 2018 to Office Action dated Sep. 19, 2018", w/English Claims, 13 pgs.
"Chinese Application Serial No. 201480027238.1, Response filed Dec. 5, 2019 to Office Action dated Sep. 26, 2019", w/ English Claims, 48 pgs.
"Chinese Application Serial No. 201480028481.5, Office Action dated Jan. 3, 2018", w/English Translation, 6 pgs.
"Chinese Application Serial No. 201480028481.5, Office Action dated Mar. 14, 2019", w/English Translation, 8 pgs.
"Chinese Application Serial No. 201480028481.5, Office Action dated Sep. 19, 2018", w/English Translation, 35 pgs.
"Chinese Application Serial No. 201480028481.5, Response filed May 8, 2018 to Office Action dated Jan. 3, 2018", w/English Claims, 17 pgs.

"Chinese Application Serial No. 201480028481.5, Response filed May 17, 2019 to Office Action dated Mar. 14, 2019", w/ English Claims, 19 pgs.
"Chinese Application Serial No. 201480028481.5, Response filed Dec. 4, 2018 to Office Action dated Sep. 19, 2018", w/ English Claims, 24 pgs.
"Cognitive and Emotional Health Project: The Healthy Brain—List of Cognitive Measures", U.S. Department of Health and Human Services, [Online]. Retrieved from the Internet: <URL: http://trans.nih.gov/CEHP/hbpcog-list.htm>, (Feb. 11, 2016), 3 pgs.
"European Application Serial No. 14770223.7, Extended European Search Report dated May 3, 2017", 23 pgs.
"European Application Serial No. 14770223.7, Partial Supplementary European Search Report dated Nov. 9, 2016", 10 pgs.
"European Application Serial No. 14770223.7, Response filed May 20, 2016 to Communication pursuant to Rules 161(2) and 162 EPC dated Nov. 11, 2015", 5 pgs.
"International Application Serial No. PCT/US2014/026962, International Preliminary Report on Patentability dated Mar. 10, 2015", 11 pgs.
"International Application Serial No. PCT/US2014/026962, International Search Report dated Aug. 5, 2014", 3 pgs.
"International Application Serial No. PCT/US2014/026962, Written Opinion dated Aug. 5, 2014", 6 pgs.
Addy, et al., "Single-dose administration of MK-0657, an NR2B-selective NMDA antagonist, does not result in clinically meaningful improvement in motor function in patients with moderate Parkinson's disease", The Journal of Clinical Pharmacology 49(7), (2009), 9 pgs.
Berendse, Henk W, et al., "Diagnosing premotor Parkinson's disease using a two-step approach combining olfactory testing and DAT SPECT imaging", Parkinsonism and Related Disorders, 15S3, [Online]. Retrieved from the Internet: <URL: http://www.ncbi.nlm.nih.gov/pubmed/20083001>, (Dec. 1, 2009), S26-S30.
Berger, et al., "The cholinergic rapid eye movement sleep induction test with RS-86: State or trait marker of depression", Archives of General Psychiatry 46.5, (1989), 8 pgs.
Boettger, M.K., et al., "Increased cold and heat pain thresholds influence the thermal grill illusion in schizophrenia", European Journal of Pain, 17(2), (2013), 200-209.
Cullen, Breda, et al., "A review of screening tests for cognitive impairment", Journal of Neurology, Neurosurgery and Psychiatry, 78(8), (Aug. 2007), 790-799.
Dawson, Geraldine, et al., "Randomized, Controlled Trial of an Intervention for Toddlers with Autism; The Early Start Denver Model", Pediatrics, 125(1), (Jan. 2010), e17-e23.
Fein, et al., "Optimal Outcome in individuals with a history of autism", The Journal of Child Psychology and Psychiatry, 54(2), (2013), 195-205.
Guskiewicz, Kevin M., et al., "Assessment of Postural Stability Following Sport Related Concussion", Current Sports Medicine Reports, 2(1), (Feb. 2003), 24-30.
Lindstedt, Fredrik, et al., "Evidence for Thalamic Involvement in the Thermal Grill Illusion: an fMRI Study", PlosOne, 6(11), e27075, (Nov. 2011), 13 pgs.
Oride, et al., "Reliability Study of the Pierce and King-Devick Saccade Tests", American Journal of Optometry and Physiological Optics, 63(6), (1985), 419-424.
Riemann, Bryan L., et al., "Relationship Between Clinical and Forceplate Measures of Postural Stability", Journal of Sport Rehabilitation, 8(2), (May 1999), 71-82.
Zhang, Daoqiang, et al., "Multimodal classification of Alzheimer's disease and mild cognitive impairment", NeuroImage, 55(3), (Jan. 5, 2011), 856-867.
U.S. Appl. No. 14/773,872, filed Sep. 9, 2015, Multi-Modal Pharmaco-Diagnostic Assessment of Brain Health.
"Canadian Application Serial No. 2,906,652, Office Action dated Apr. 8, 2020", 5 pgs.
"Chinese Application Serial No. 201480027238,1, Decision of Rejection dated May 22, 2020", W/English Translation, 12 pgs.

(56) References Cited

OTHER PUBLICATIONS

"U.S. Appl. No. 14/773,872, Response filed Mar. 31, 2020 to Non Final Office Action dated Dec. 31, 2019", 26 pgs.

* cited by examiner

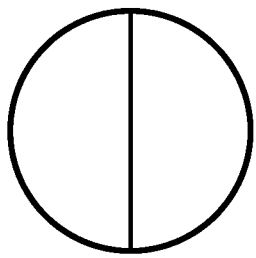 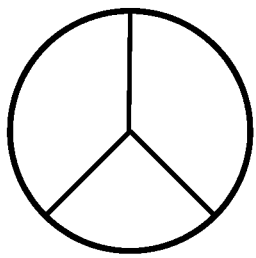 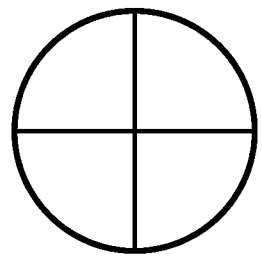
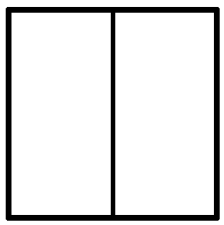 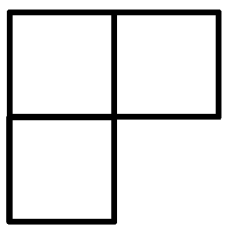 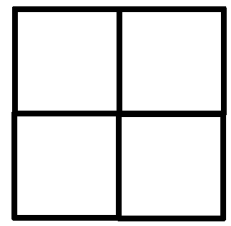
Fig. 9A    Fig. 9B    Fig. 9C
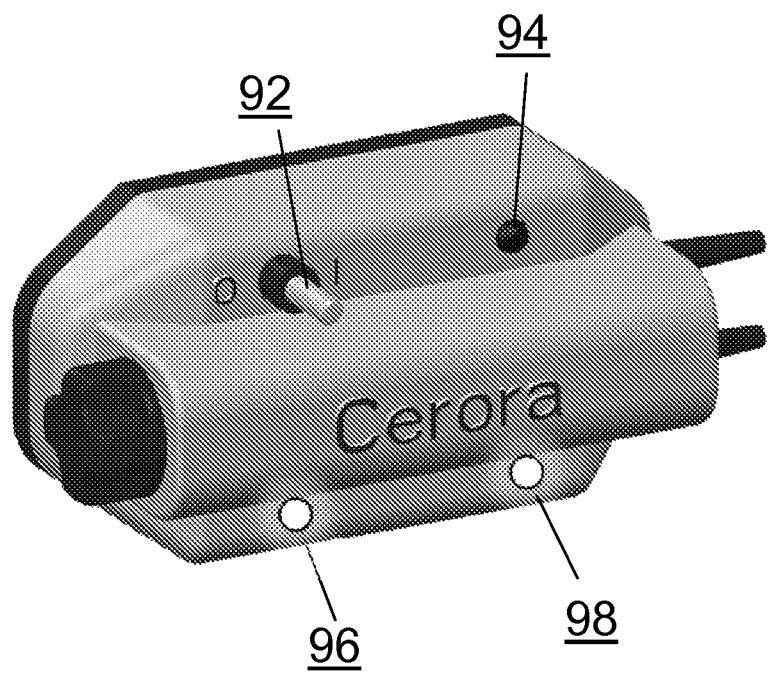
Fig. 10

A system and diagnostic signatures which are derived
SYSTEM AND SIGNATURES FOR THE MULTI-MODAL PHYSIOLOGICAL STIMULATION AND ASSESSMENT OF BRAIN HEALTH

CROSS-REFERENCE TO RELATED APPLICATIONS

This application is the National Stage of International Application No. PCT/US2014/028061, filed Mar. 14, 2014, which claims the benefit of U.S. Provisional Application No. 61/799,842, filed Mar. 15, 2013; U.S. Provisional Application No. 61/836,294, filed Jun. 18, 2013; and U.S. Provisional Application No. 61/932,915, filed Jan. 29, 2014, the entire disclosures of which are incorporated herein by reference.

TECHNICAL FIELD

The invention relates to diagnosis and analysis of brain health through the use of activated tasks and stimuli in a system to dynamically assess one's brain state and function.

BACKGROUND

Normal functioning of the brain and central nervous system is critical to a healthy, enjoyable and productive life. Disorders of the brain and central nervous system are among the most dreaded of diseases. Many neurological disorders such as stroke, Alzheimer's disease, and Parkinson's disease are insidious and progressive, becoming more common with increasing age. Others such as schizophrenia, depression, multiple sclerosis and epilepsy arise at younger age and can persist and progress throughout an individual's lifetime. Sudden catastrophic damage to the nervous system, such as brain trauma, infections and intoxications can also affect any individual of any age at any time.

Most nervous system dysfunction arises from complex interactions between an individual's genotype, environment and personal habits and thus often presents in highly personalized ways. However, despite the emerging importance of preventative health care, convenient means for objectively assessing the health of one's own nervous system have not been widely available. Therefore, new ways to monitor the health status of the brain and nervous system are needed for normal health surveillance, early diagnosis of dysfunction, tracking of disease progression and the discovery and optimization of treatments and new therapies.

Unlike cardiovascular and metabolic disorders, where personalized health monitoring biomarkers such as blood pressure, cholesterol, and blood glucose have long become household terms, no such convenient biomarkers of brain and nervous system health exist. Quantitative neurophysiological assessment approaches such as positron emission tomography (PET), functional magnetic resonance imaging (fMRI) and neuropsychiatric or cognition testing involve significant operator expertise, inpatient or clinic-based testing and significant time and expense. One potential technique that may be adapted to serve a broader role as a facile biomarker of nervous system function is a multi-modal assessment of the brain from a number of different forms of data, including electroencephalography (EEG), which measures the brain's ability to generate and transmit electrical signals. However, formal lab-based EEG approaches typically require significant operator training, cumbersome equipment, and are used primarily to test for epilepsy.

Alternate and innovative biomarker approaches are needed to provide quantitative measurements of personal brain health that could greatly improve the prevention, diagnosis and treatment of neurological and psychiatric disorders. Unique multi-modal devices and tests that lead to biomarkers of Parkinson's disease, Alzheimer's disease, concussion and other neurological and neuropsychiatric conditions is a pressing need.

SUMMARY

A system and diagnostic signatures which are derived from the data collected in the system address the above needs in the art by capturing multiple streams of biological sensor data for assessing brain health and functionality of a user. In an exemplary embodiment, the system includes a plurality of biological sensors adapted to collect biological sensor data from the user as well as the ability to stimulate the brain in a variety of sensory, cognitive, physical, and chemical challenges. The biological sensors include an active brainwave sensor that collects at least one channel of EEG brainwave data in addition to one or more additional biological sensor data streams selected from among accelerometer measures of balance and movement, microphone measurements of voice and response, image sensor to track eye movement and biometric identification, pulse oximetry measurements of heart rate, heart rate variability, and arterial oxygen, Galvanic Skin Response (or Dermal Skin Conductance) for emotional and mood information, cognitive data in the form of key strokes, and mouse clicks or touch screen events during cognitive challenges. Lastly, regulatory agency approved drugs, ingredients, and compounds can be administered in a diagnostic capacity to challenge the brain and diagnostically measure the response.

In one embodiment, the system includes only one reusable electronic module (REM) module proximal to the brain for recording various biological signal streams of data. This is complemented by various biological signal streams collected simultaneously in a peripheral MCU in the form of a laptop computer, tablet PC or smartphone like device.

In another embodiment, the system includes one or more REM module(s) in addition to the REM module on the head. In this embodiment, a non-head REM module is positioned on the trunk of the human subject to collect position and heart rate information or, alternatively, or in addition, placed on the wrist or ankle of a limb in order to record biological signals from the extremities of the individual. In all cases, the data are co-registered in time so that each modality or biological signal can be analyzed either alone in isolation or in a cross correlative fashion. Multi-variate predictive statistical models can be built with the diagnostic information to help the health and wellness of the human subject under assessment.

The system also has the means to stimulate the human subject under assessment for their response to sensory, cognitive, physical, and chemical challenges. In one embodiment of the invention, the visual system is assessed with either (i) photic stimulation from either a peripheral MCU or head REM or (ii) images or movies displayed on the video screen of a peripheral MCU. In another embodiment, the auditory system is challenged with binaural beats, mono aural beats, isochronic tones or other important auditory stimulation with a known or expected biomarker signature within the multi-modal streams of data. In another embodiment, the gastronomic system is stimulated with either a dose of specialized food product for consumption or, alternatively, directly with a tongue electrical stimulation device. In yet another embodiment, the olfactory system is stimulated via scratch and sniff cards, automated aroma delivery systems or direct electrical stimulation of the olfactory bulb. Lastly, the sense of touch can be stimulated via known textures or through direct transcutaneous electrical stimulation. It is part of the present invention that any of these embodiments can be practiced alone or in combination as may be desired and advantageous.

An alternate embodiment of the invention includes various multi-contact electrodes whereby a standard circle or square is equally divided into 2, 3 or 4 equivalent but independent electrodes. In doing so, a 2 electrode system of the present invention may become a 4, 6 or 8 electrode system within the same spatial and temporal configuration, including the form factor of a headband.

One embodiment includes the use of a disposable air pillow or cushion or other compact yet expandable device to create an irregular or unstable surface for human subjects to try to balance on to assess static balance/stability or move across to assess dynamic balance/stability.

In another embodiment, additional data transducers are built into the REM module such that the system can acquire diverse streams of biological sensor data. One particular embodiment includes the inclusion of either an acoustic microphone and/or a forward facing digital image sensor (essentially a movie camera).

Another embodiment includes use of either an image sensor for image processing derived eye tracking and movement or a more dedicated device or technology, much like the Google Glass eye-tracker or an infra-red based eye tracker.

In another embodiment, the REM is designed with a mass storage device such as a microSD card or other high density RAM storage unit. This RAM storage unit enables data collection from the REM directly to mass storage without the need for a wireless connection to a peripheral MCU.

In yet another embodiment of the invention, photographic images with unique emotional and valence based characteristics are shown to human subjects while their biological signals are measured and recorded. In this case, those without normal emotional response to fanciful images (a pig flying over an ocean) can be objectively detected by the biological sensor data streams. Other mood and emotional information can be advantageously collected. In one particular embodiment, galvanic skin response (GSR) measurements are gathered at the same time that brainwave EEG and accelerometer measurements are collected while photographic images are presented. This could equally work for dynamic images such as movies rather than static images.

BRIEF DESCRIPTION OF THE DRAWINGS

Embodiments of the invention can be better understood with reference to the following drawings.

FIG. 9A is a schematic illustration of single circular or square electrode that has been divided into two equivalent but adjacent electrodes in the same amount of space.

FIG. 9B is a schematic illustration of single circular or square electrode that has been divided into three equivalent adjacent electrodes in the same amount of space.

FIG. 9C is a schematic illustration of single circular or square electrode that has been divided into four equivalent adjacent electrodes in the same amount of space.

FIG. 10 is a schematic illustration of a headband supported electronics module with both a microphone and small camera embedded into the module.

appear cognitively intact while several subjects appear to exhibit cognitive issues consistent with concussion.

Figure 22:
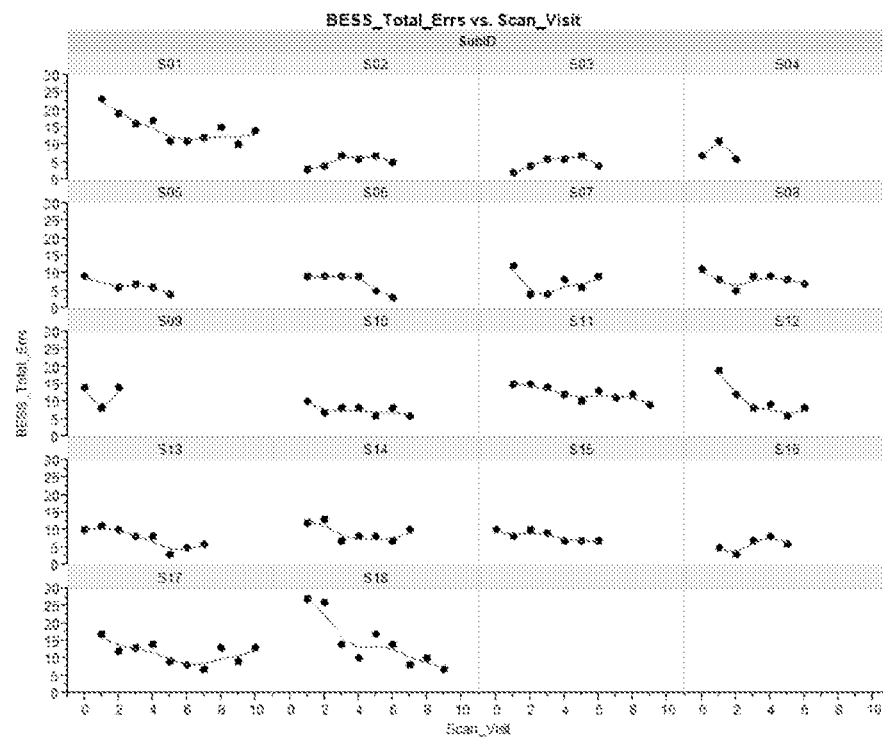

FIG. 22 is a graphical representation of the Balance Error Scoring System (BESS) total error score (along the y-axis) upon serial assessment at several different scans noted along the x-axis as scan visit for N=18 eighteen subjects. Flat trajectories appear near zero (a perfect score) appear stable within their vestibular system while several subjects appear to exhibit balance and vestibular issues consistent with concussion.

Figure 23:
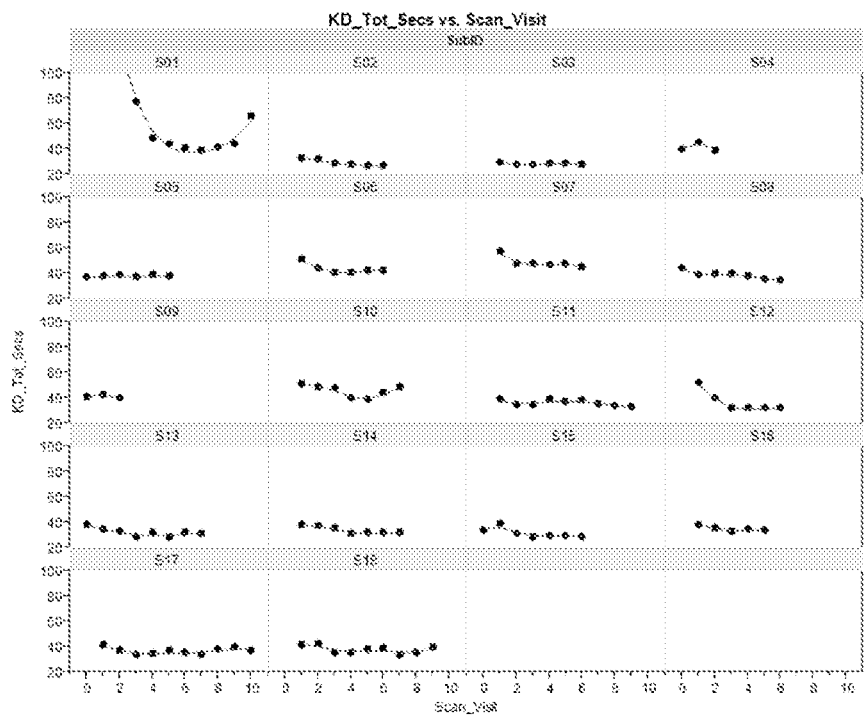

FIG. 23 is a graphical representation of the King-Devick Ophthalmologic Test (Oride et al 1986) measured in total time across three test cards (sec) with minimal errors (along the y-axis) upon serial assessment at several different scans noted along the x-axis as scan visit for N=18 eighteen subjects. Flat trajectories near forty seconds appear as consistent and stable neuro-ophthalmological processing while several subjects appear to exhibit longer times at early scan visits consistent with concussion.

Figure 24:
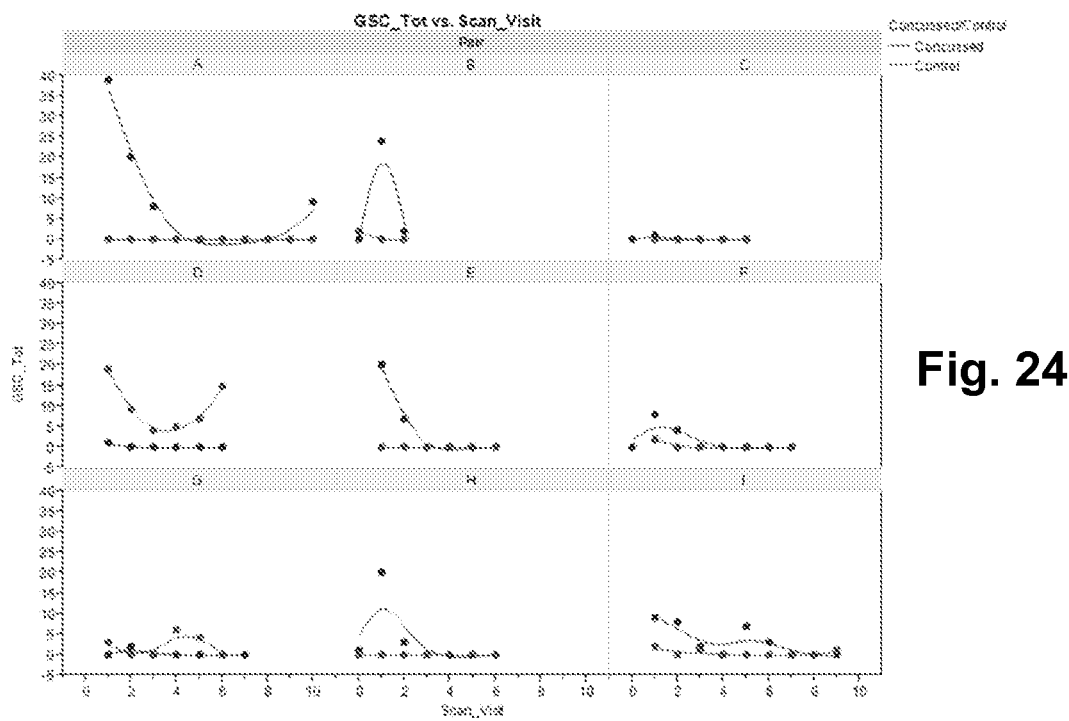

FIG. 24 is a graphical representation of the Graded Symptom Checklist total score (along the y-axis) upon serial assessment at several different scans noted along the x-axis as scan visit for N=18 eighteen subjects. Subjects are paired as concussed (red traces) or the non-injured team mate (green traces) who followed the same scan sequence to serve as a control.

Figure 25:
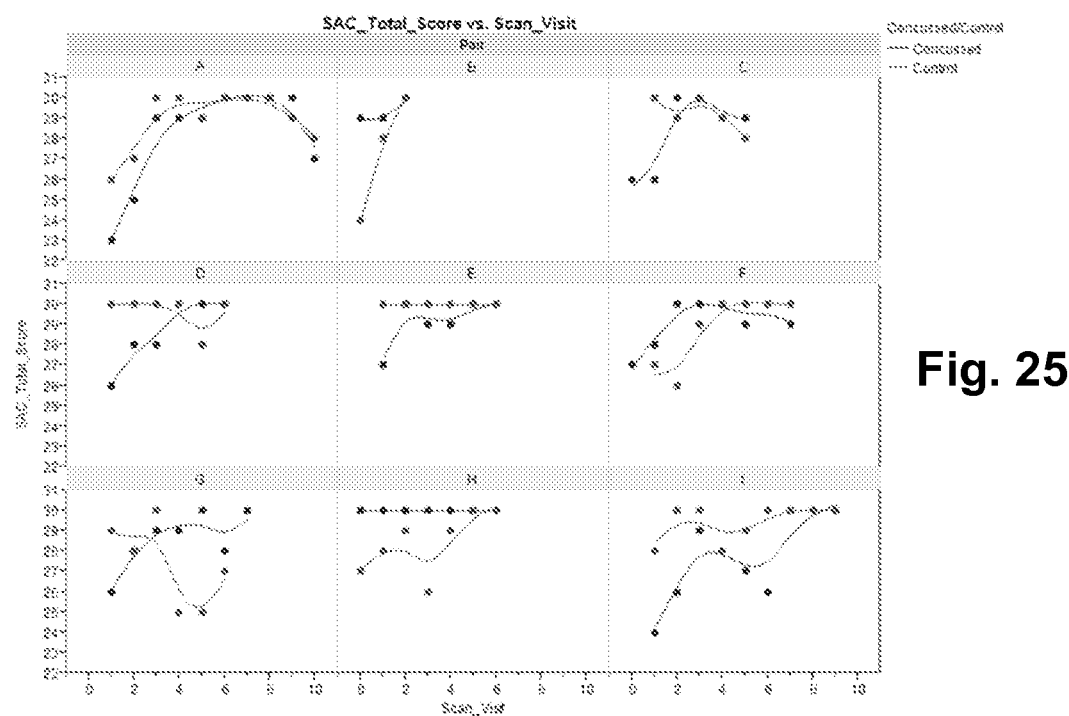

FIG. 25 is a graphical representation of the Standard Assessment of Concussion (SAC) total score (along the y-axis) upon serial assessment at several different scans noted along the x-axis as scan visit for N=18 eighteen subjects. Subjects are paired as concussed (red traces) or the non-injured team mate (green traces) who followed the same scan sequence to serve as a control.

Figure 26:
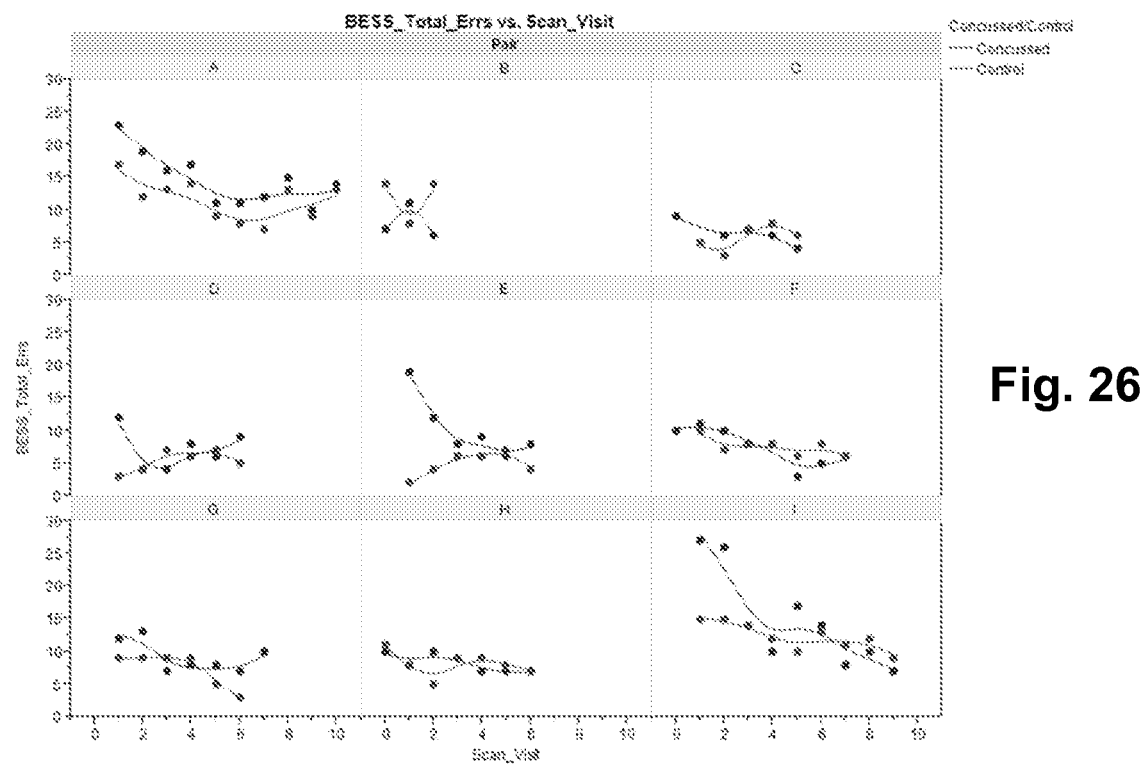

FIG. 26 is a graphical representation of the Balance Error Scoring System (BESS) total error score (along the y-axis) upon serial assessment at several different scans noted along the x-axis as scan visit for N=18 eighteen subjects. Subjects are paired as concussed (red traces) or the non-injured team mate (green traces) who followed the same scan sequence to serve as a control.

Figure 27:
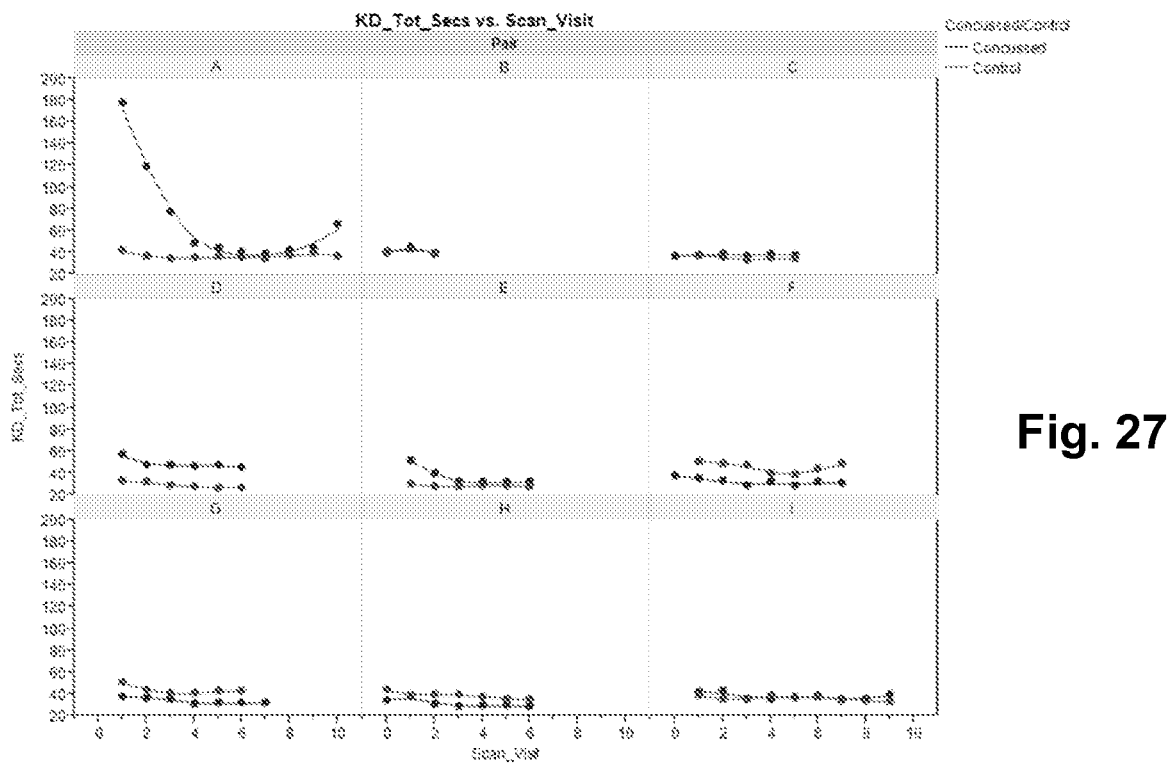

FIG. 27 is a graphical representation of the King-Devick Ophthalmologic Test (Oride et al 1986) measured in total time across three test cards (sec) with minimal errors (along the y-axis) upon serial assessment at several different scans noted along the x-axis as scan visit for N=18 eighteen subjects. Subjects are paired as concussed (red traces) or the non-injured team mate (green traces) who followed the same scan sequence to serve as a control.

Figure 28:
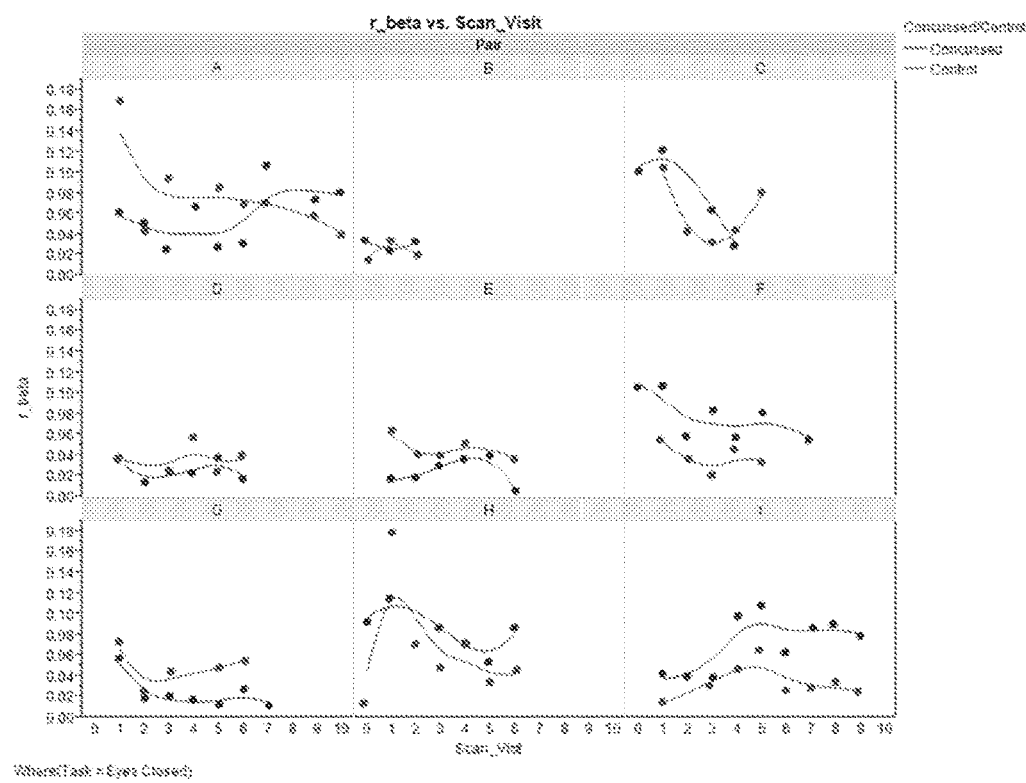

FIG. 28 is a graphical representation of the relative beta brainwave power during an eyes closed task (along the y-axis) upon serial assessment at several different scans noted along the x-axis as scan visit for N=18 eighteen subjects. Subjects are paired as concussed (red traces) or the non-injured team mate (green traces) who followed the same scan sequence to serve as a control.

Figure 29:
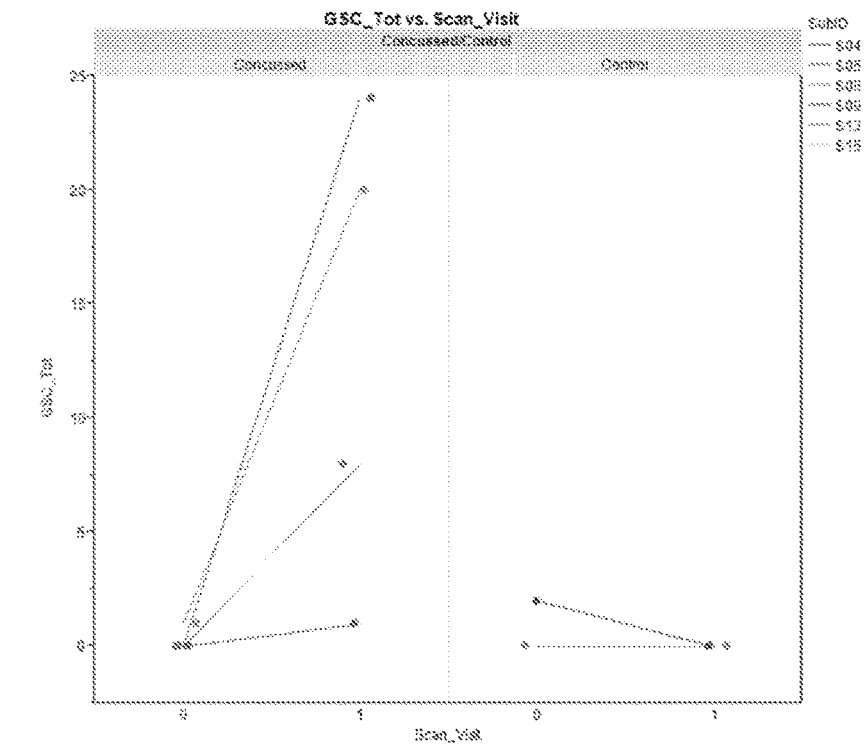

FIG. 29 is a graphical representation of the Graded Symptom Checklist total score (along the y-axis) upon serial assessment at baseline (scan visit 0) and scan visit 1 (along the x-axis) for N=6 six subjects who had a baseline. Concussed athletes are in the left panel and non-injured teammate controls are in the right panel.

Figure 30:
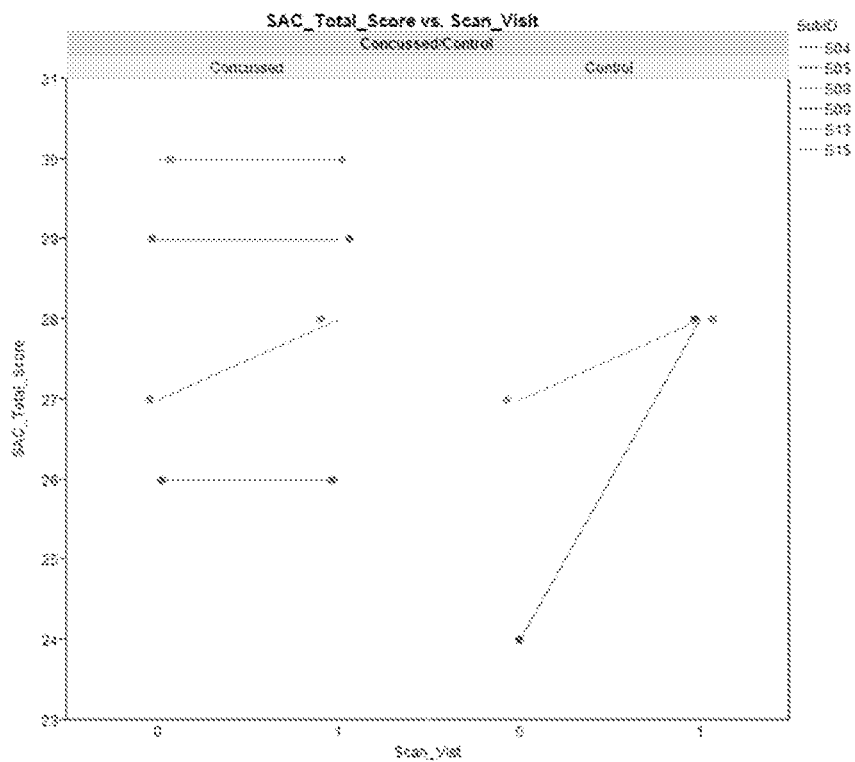

FIG. 30 is a graphical representation of the Standard Assessment of Concussion (SAC) total score (along the y-axis) upon serial assessment at baseline (scan visit 0) and scan visit 1 (along the x-axis) for N=6 six subjects who had a baseline. Concussed athletes are in the left panel and non-injured teammate controls are in the right panel.

Figure 31:
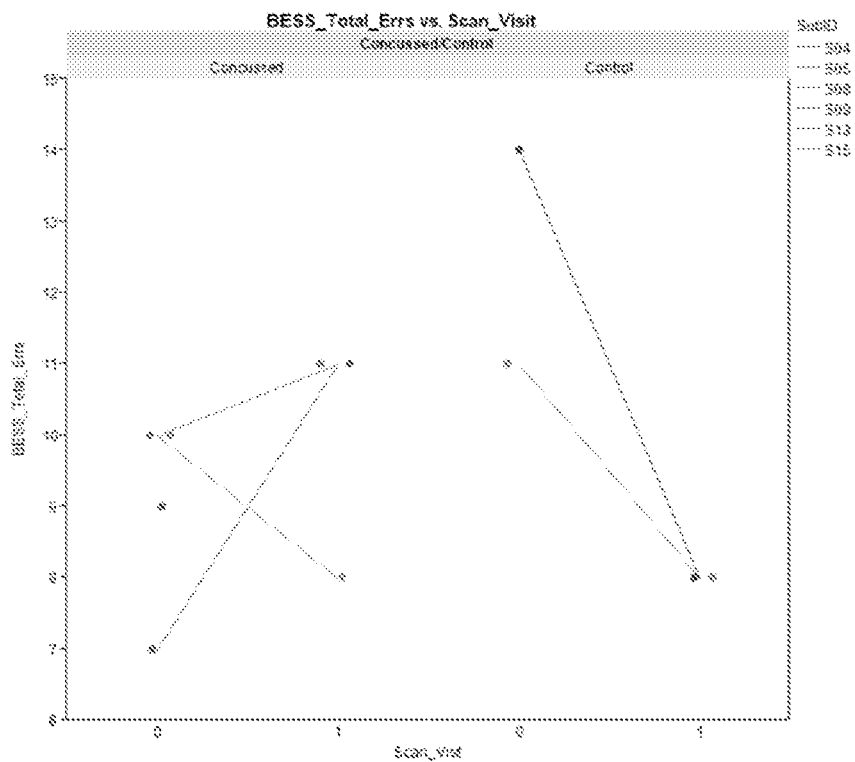

FIG. 31 is a graphical representation of the Balance Error Scoring System (BESS) total error score (along the y-axis) upon serial assessment at baseline (scan visit 0) and scan visit 1 (along the x-axis) for N=6 six subjects who had a baseline. Concussed athletes are in the left panel and non-injured teammate controls are in the right panel.

Figure 32:
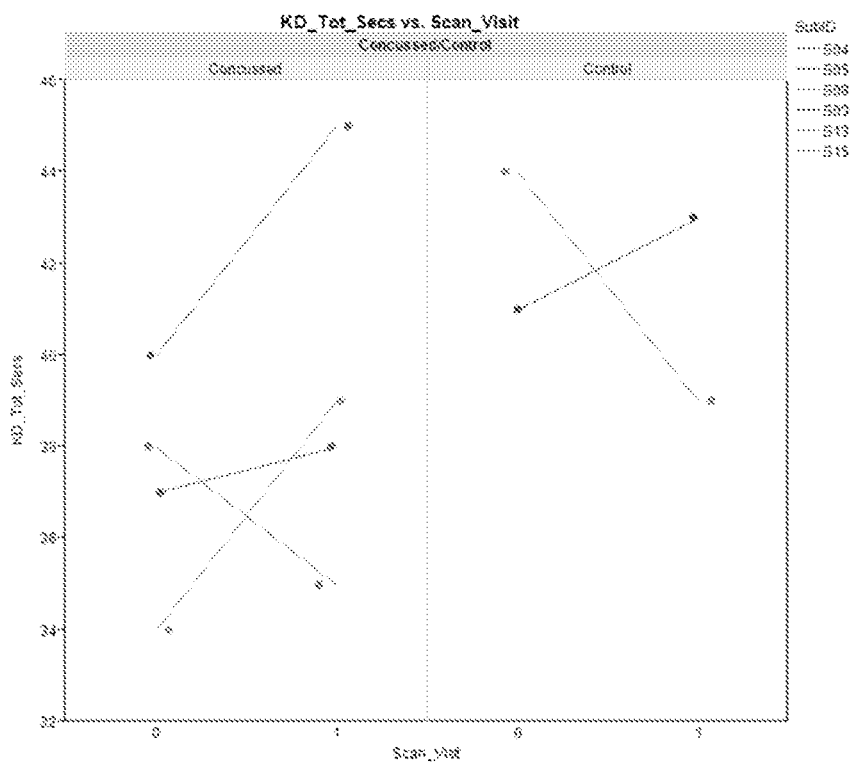

FIG. 32 is a graphical representation of the King-Devick Ophthalmologic Test (Oride et al 1986) measured in total time across three test cards (sec) with minimal errors (along the y-axis) upon serial assessment at baseline (scan visit 0) and scan visit 1 (along the x-axis) for N=6 six subjects who had a baseline. Concussed athletes are in the left panel and non-injured teammate controls are in the right panel.

Figure 33:
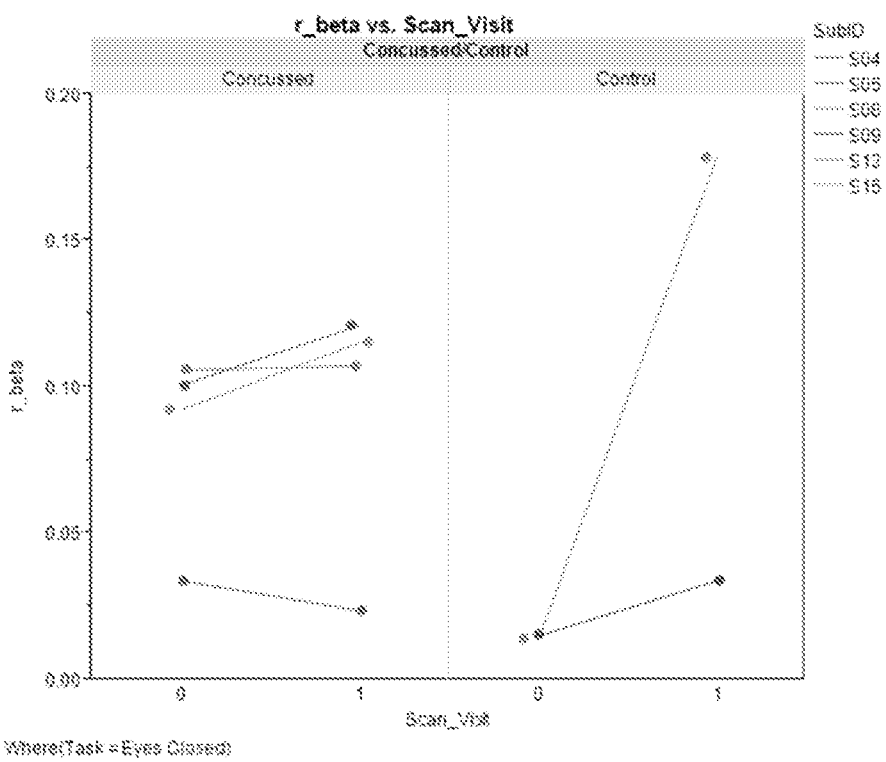

FIG. 33 is a graphical representation of the relative beta brainwave power during an eyes closed task (along the y-axis) upon serial assessment at baseline (scan visit 0) and scan visit 1 (along the x-axis) for N=6 six subjects who had a baseline. Concussed athletes are in the left panel and non-injured teammate controls are in the right panel.

Figure 34:
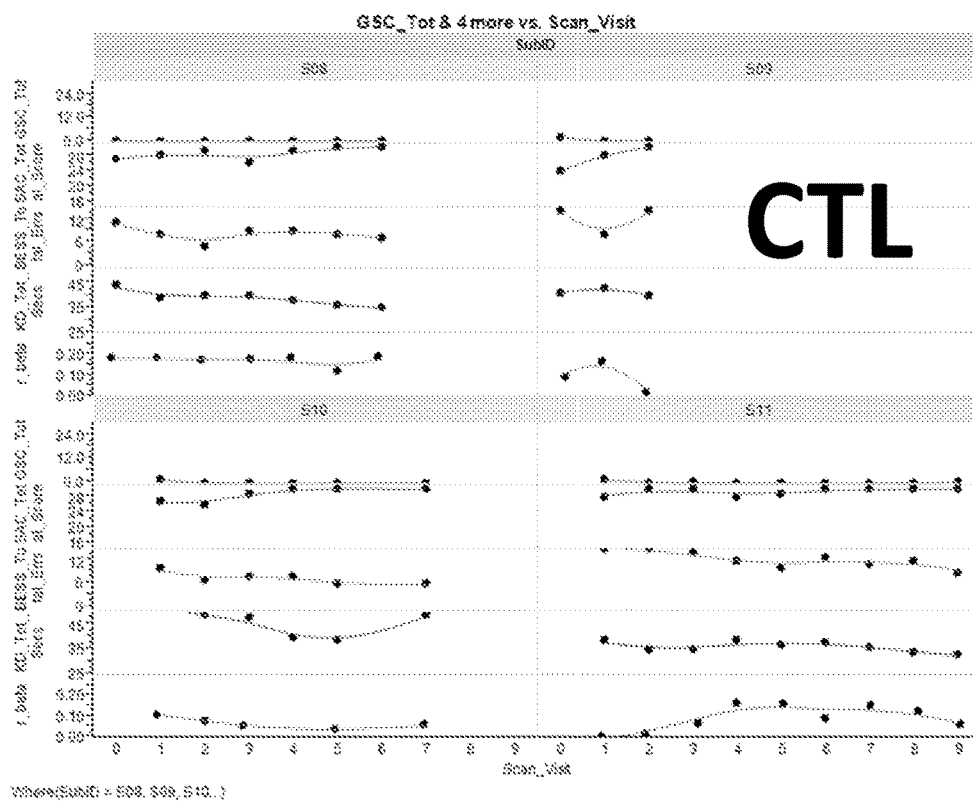

FIG. 34 is a graphical representation of 4 non-injured control (CTL) subjects whereby the GSC, SAC, BESS, KD time, and relative beta power (along the y-axis) are each individually stacked on top of each for each scan visit (along the x-axis). This is useful in Return To Play decision making.

Figure 35:
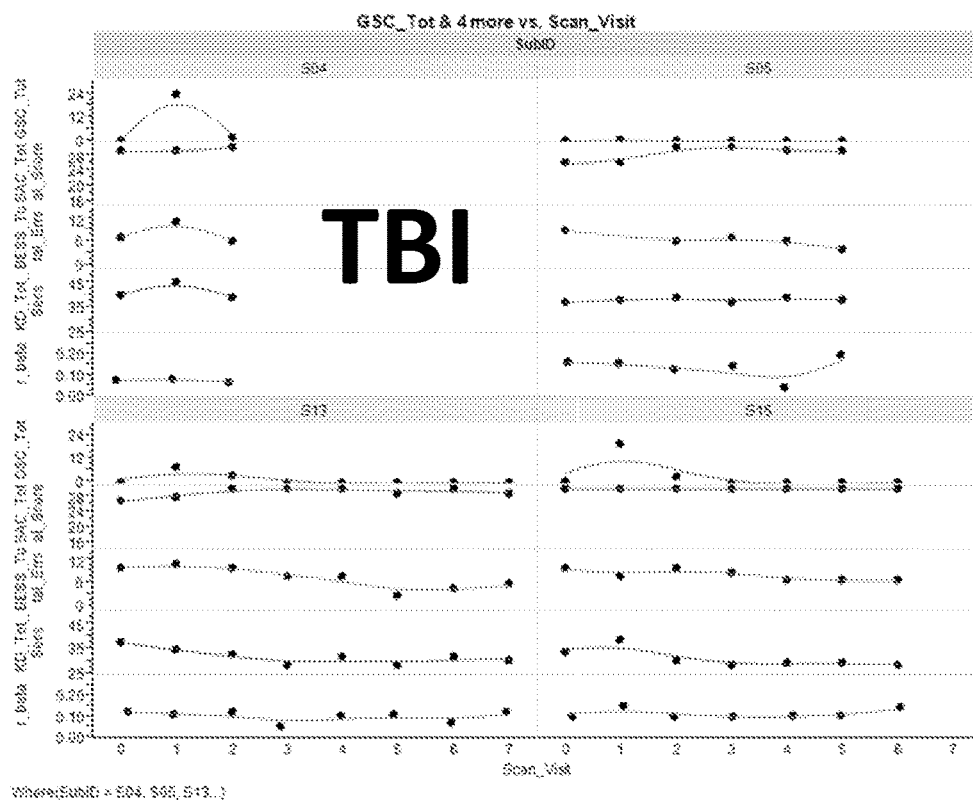

FIG. 35 is a graphical representation of 4 concussed (TBI) subjects whereby the GSC, SAC, BESS, KD time, and relative beta power (along the y-axis) are each individually stacked on top of each for each scan visit (along the x-axis). This is useful in Return To Play decision making.

Figure 36:
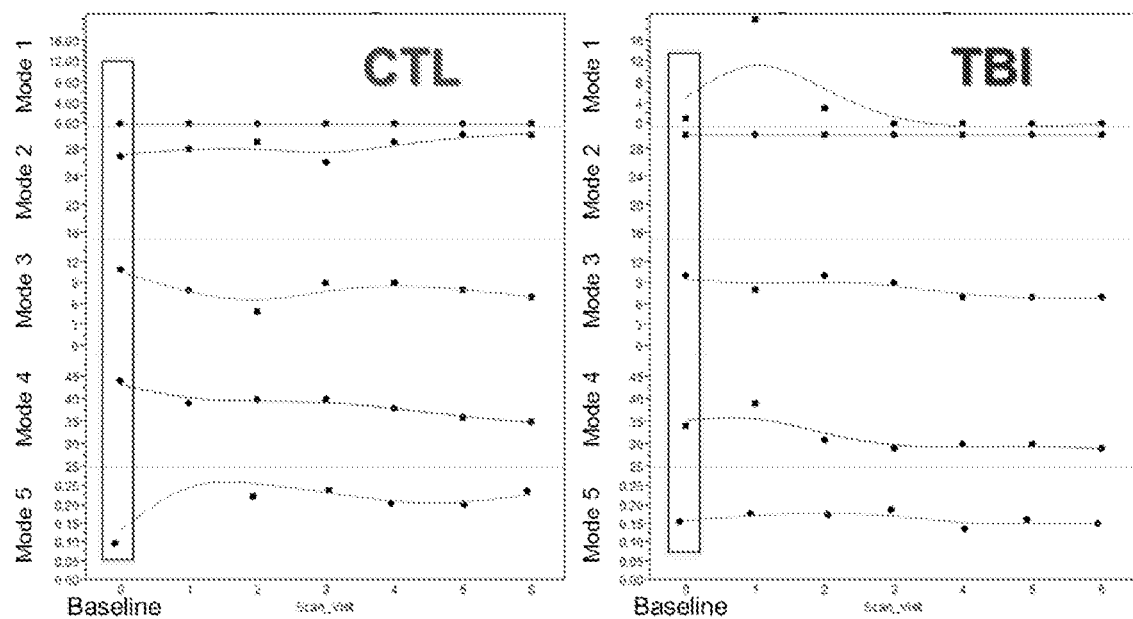

FIG. 36 is a graphical representation of 1 non-injured control (CTL) subject and 1 concussed teammate (TBI) whereby the GSC, SAC, BESS, KD time, and relative beta power (along the y-axis) are each individually stacked on top of each for each scan visit (along the x-axis). This is useful in Return To Play decision making.

Figure 37:
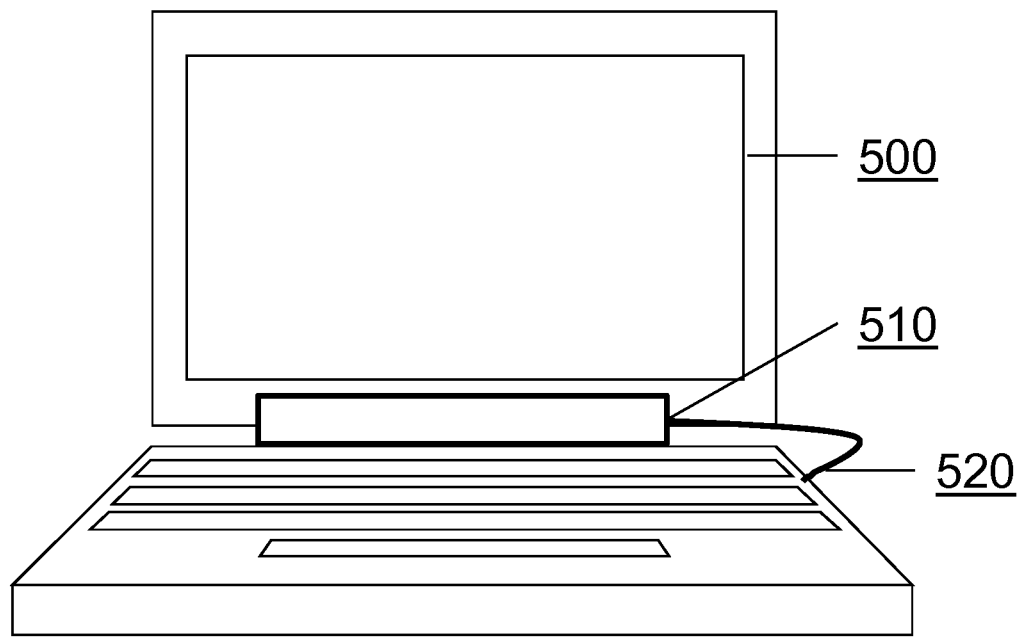

FIG. 37 is a schematic illustration of laptop or tablet PC. An external eye tracker is shown below the video monitor and connects either via wire (e.g. USB) or wirelessly (e.g. Bluetooth, ZigBee, WiFi).

Figure 38:
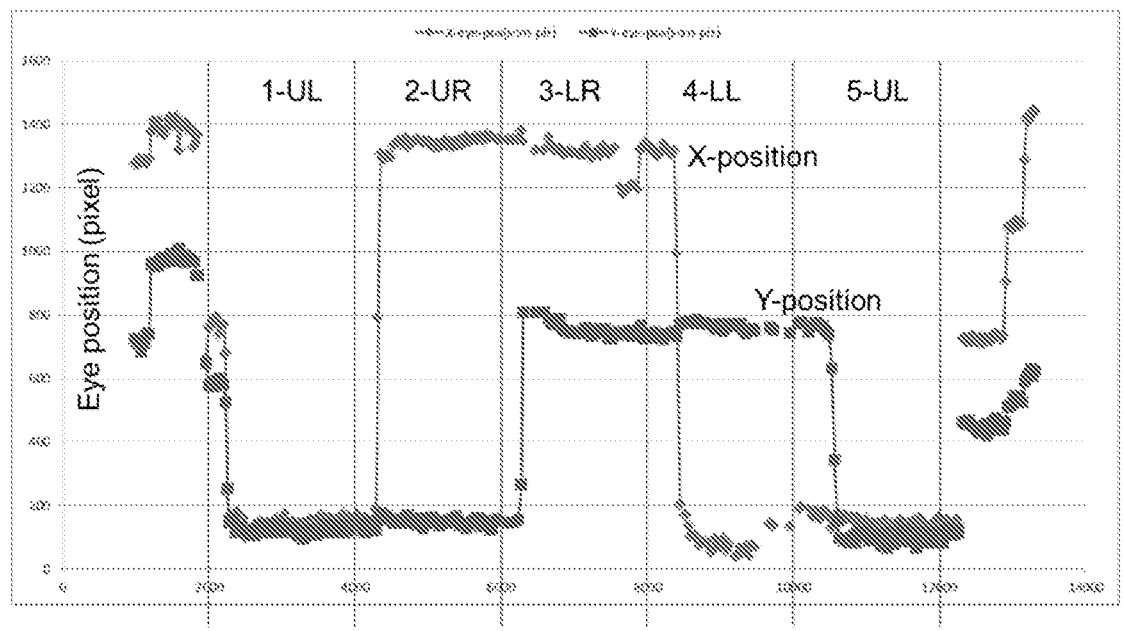

FIG. 38 is a graphical representation of the output of a 30 Hz eye tracker when a series of cards are presented which moves the eye around the corners of the screen from top-left to top-right to bottom-right to bottom-left to top-left again. The origin for the coordinate system is the upper left of the computer screen.

Figure 39:
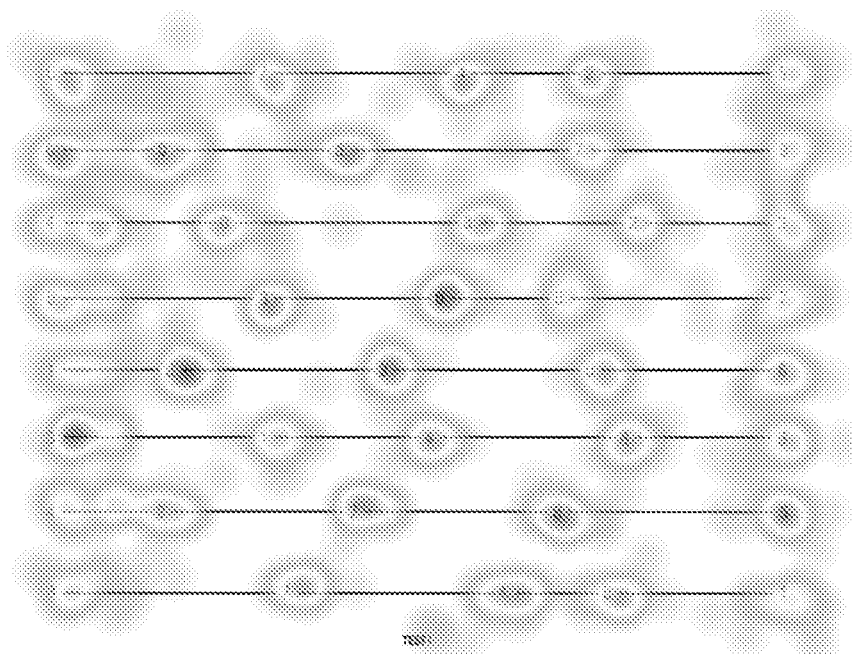

FIG. 39 is a graphical heat map representation of the amount of time the eyes of study subjects spent focused on the numbers on the stimuli cards. This data supplements the brainwave, voice and neuropsychology data.

Figure 40:
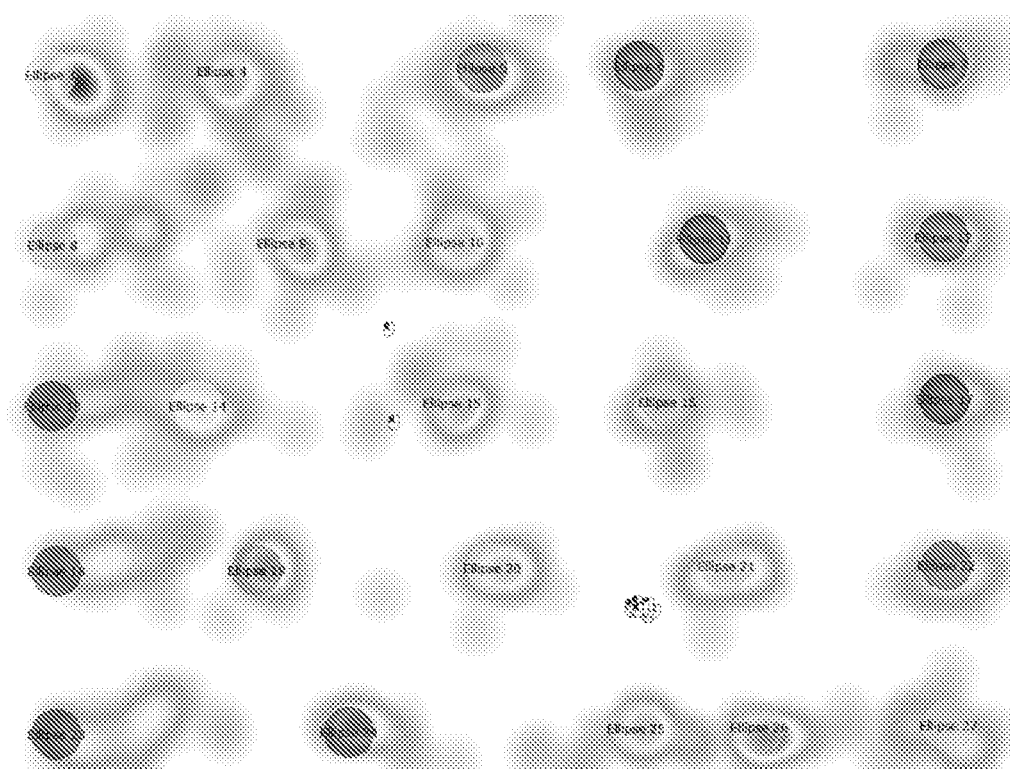

FIG. 40 is a graphical heat map representation of the amount of time the eyes of study subjects spent focused on the numbers on the stimuli cards. This drawing also illustrates the Areas of Interest that have been created which enables determination of how much time was spent within an AOI versus outside various AOIs. This data supplements the brainwave, voice and neuropsychology data.

Figure 41:
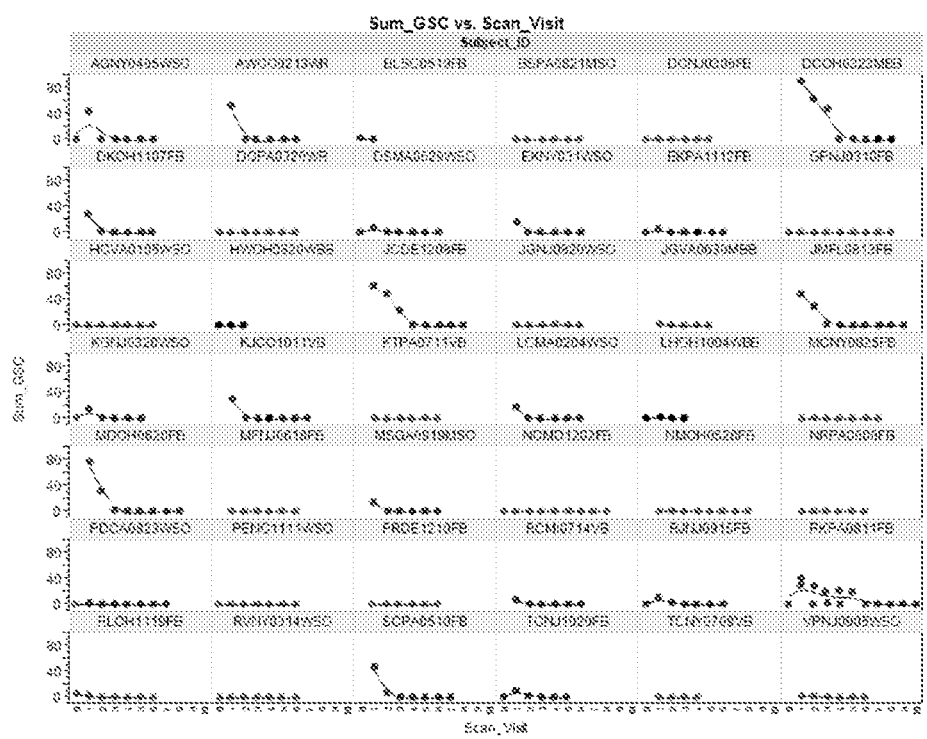

FIG. 41 is a graphical representation of the Graded Symptom Checklist total score (along the y-axis) upon serial assessment at several different scans noted along the x-axis as scan visit for N=40 eighteen subjects. Flat trajectories appear free from symptoms while several subjects appear to exhibit symptoms consistent with concussion.

Figure 42:
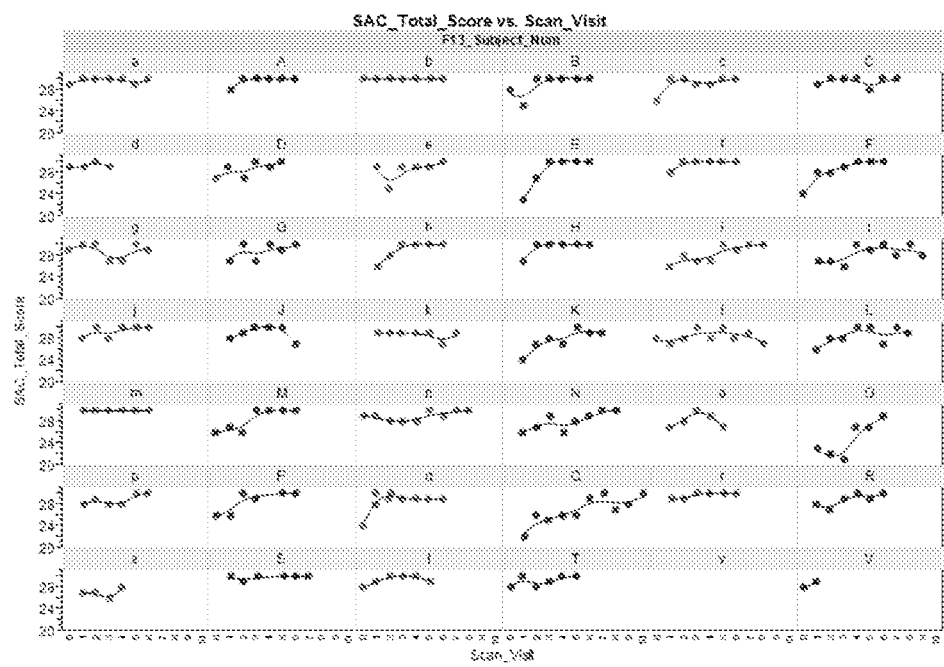

FIG. 42 is a graphical representation of the Standard Assessment of Concussion (SAC) total score (along the y-axis) upon serial assessment at several different scans noted along the x-axis as scan visit for N=40 eighteen subjects. Flat trajectories appear near 30 (a perfect score)

and appear cognitively intact while several subjects appear to exhibit cognitive issues consistent with concussion.

Figure 43:
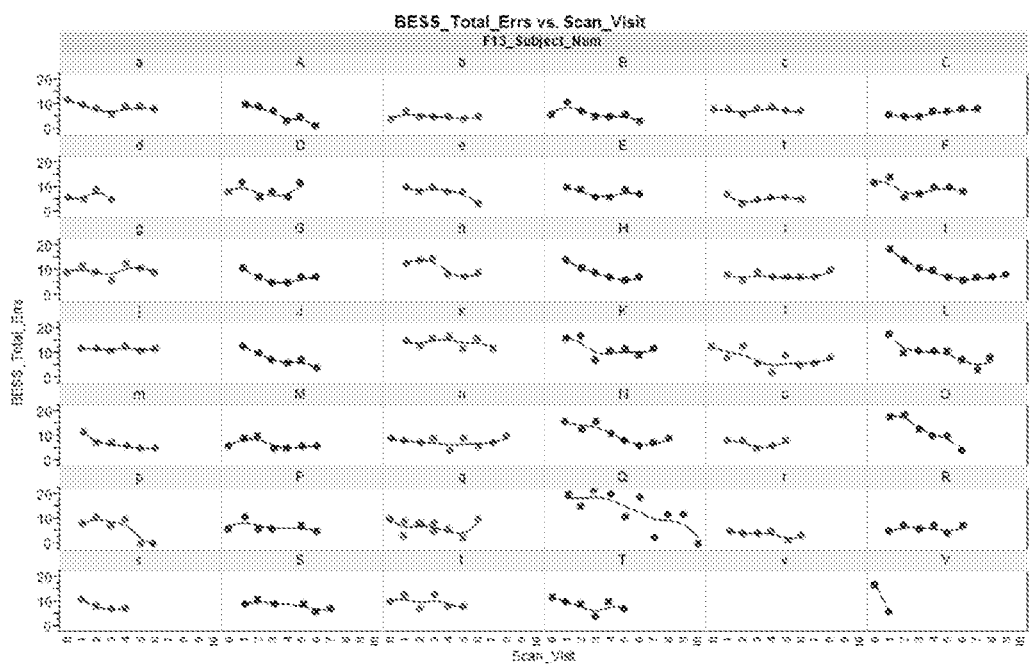

FIG. 43 is a graphical representation of the Balance Error Scoring System (BESS) total error score (along the y-axis) upon serial assessment at several different scans noted along the x-axis as scan visit for N=40 eighteen subjects. Flat trajectories appear near zero (a perfect score) and appear stable within their vestibular system while several subjects appear to exhibit balance and vestibular issues consistent with concussion.

Figure 44:
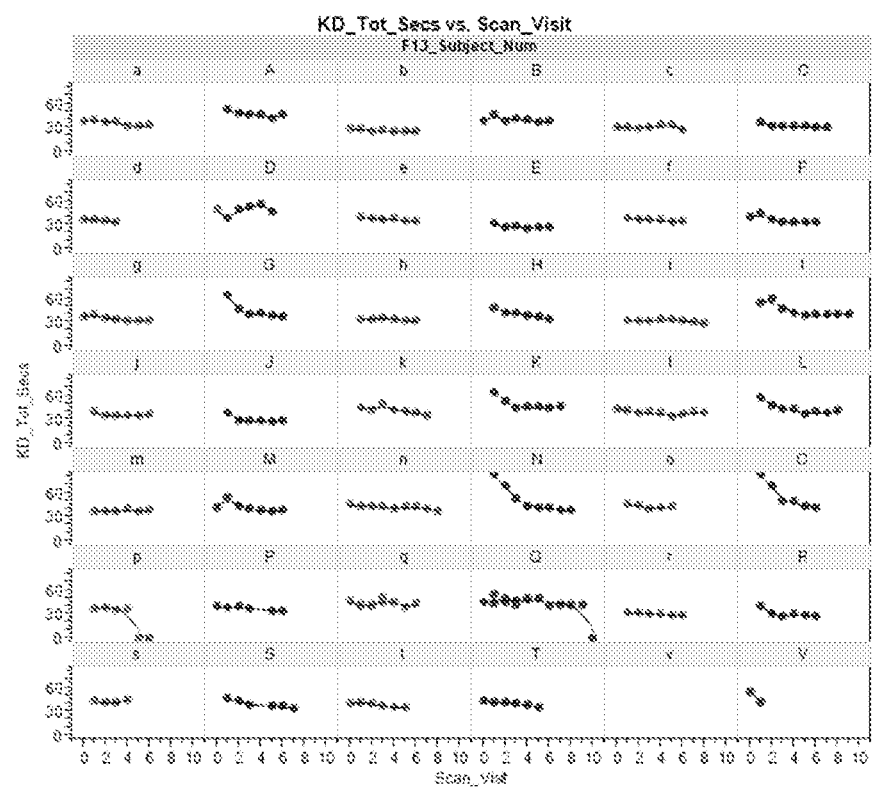

FIG. 44 is a graphical representation of the King-Devick Ophthalmologic Test (Oride et al 1986) measured in total time across three test cards (sec) with minimal errors (along the y-axis) upon serial assessment at several different scans noted along the x-axis as scan visit for N=40 eighteen subjects. Flat trajectories near forty seconds appear as consistent and stable neuro-ophthalmological processing while several subjects appear to exhibit longer times at early scan visits consistent with concussion.

Figure 45:
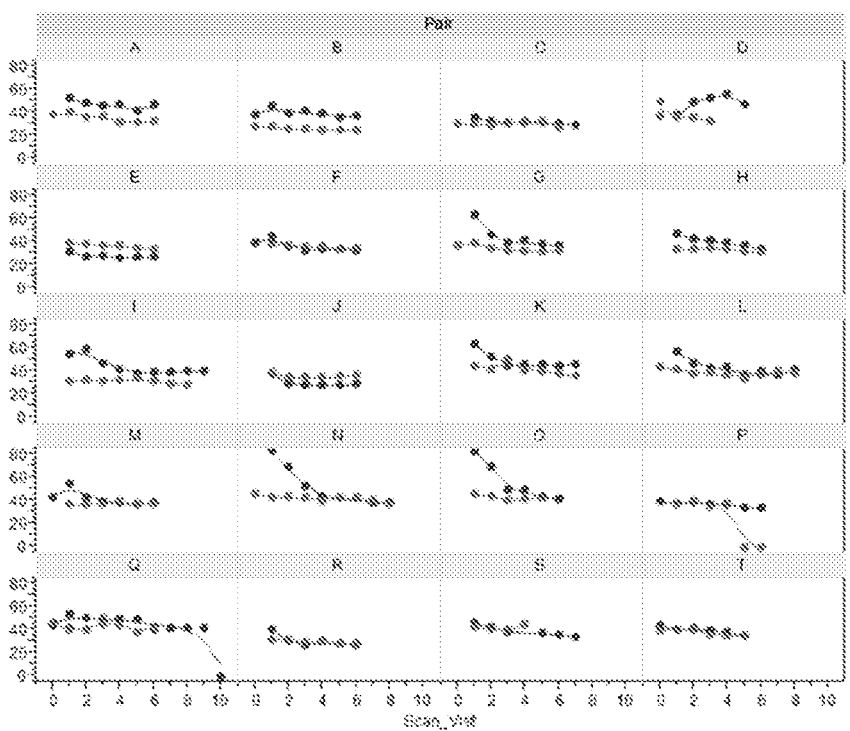

FIG. 45 is a graphical representation of the King-Devick Ophthalmologic Test (Oride et al 1986) measured in total time across three test cards (sec) with minimal errors (along the y-axis) upon serial assessment at several different scans noted along the x-axis as scan visit for N=40 eighteen subjects shown in pairs that match a non-injured athlete with an injured athlete. Flat trajectories near forty seconds appear as consistent and stable neuro-ophthalmological processing while several subjects appear to exhibit longer times at early scan visits consistent with concussion.

DETAILED DESCRIPTION OF ILLUSTRATIVE EMBODIMENTS

The invention will be described in detail below with reference to FIGS. 1-45. Those skilled in the art will appreciate that the description given herein with respect to those figures is for exemplary purposes only and is not intended in any way to limit the scope of the invention. All questions regarding the scope of the invention may be resolved by referring to the appended claims.

Definitions

By "electrode to the scalp" we mean to include, without limitation, those electrodes requiring gel, dry electrode sensors, contactless sensors and any other means of measuring the electrical potential or apparent electrical induced potential by electromagnetic means.

By "monitor the brain and nervous system" we mean to include, without limitation, surveillance of normal health and aging, the early detection and monitoring of brain dysfunction, monitoring of brain injury and recovery, monitoring disease onset, progression and response to therapy, for the discovery and optimization of treatment and drug therapies, including without limitation, monitoring investigational compounds and registered pharmaceutical agents, as well as the monitoring of illegal substances and their presence or influence on an individual while driving, playing sports, or engaged in other regulated behaviors.

A "medical therapy" as used herein is intended to encompass any form of therapy with potential medical effect, including, without limitation, any pharmaceutical agent or treatment, compounds, biologics, medical device therapy, exercise, biofeedback or combinations thereof.

By "EEG data" we mean to include without limitation the raw time series, any spectral properties determined after Fourier transformation, any nonlinear properties after nonlinear analysis, any wavelet properties, any summary biometric variables and any combinations thereof.

A "sensory and cognitive challenge" as used herein is intended to encompass any form of sensory stimuli (to the five senses), cognitive challenges (to the mind), and other challenges (such as a respiratory $CO_2$ challenge, virtual reality balance challenge, hammer to knee reflex challenge, etc.).

A "sensory and cognitive challenge state" as used herein is intended to encompass any state of the brain and nervous system during the exposure to the sensory and cognitive challenge.

An "electronic system" as used herein is intended to encompass, without limitation, hardware, software, firmware, analog circuits, DC-coupled or AC-coupled circuits, digital circuits, FPGA, ASICS, visual displays, audio transducers, temperature transducers, olfactory and odor generators, or any combination of the above.

By "spectral bands" we mean without limitation the generally accepted definitions in the standard literature conventions such that the bands of the PSD are often separated into the Delta band ($f<4$ Hz), the Theta band ($4<f<7$ Hz), the Alpha band ($8<f<12$ Hz), the Beta band ($12<f<30$ Hz), and the Gamma band ($30<f<100$ Hz). The exact boundaries of these bands are subject to some interpretation and are not considered hard and fast to all practitioners in the field.

By "calibrating" we mean the process of putting known inputs into the system and adjusting internal gain, offset or other adjustable parameters in order to bring the system to a quantitative state of reproducibility.

By "conducting quality control" we mean conducting assessments of the system with known input signals and verifying that the output of the system is as expected. Moreover, verifying the output to known input reference signals constitutes a form of quality control which assures that the system was in good working order either before or just after a block of data was collected on a human subject.

By "biomarker" we mean an objective measure of a biological or physiological function or process.

By "biomarker features or metrics" we mean a variable, biomarker, metric or feature which characterizes some aspect of the raw underlying time series data. These terms are equivalent for a biomarker as an objective measure and can be used interchangeably.

By "non-invasively" we mean lacking the need to penetrate the skin or tissue of a human subject.

By "diagnosis" we mean any one of the multiple intended use of a diagnostic including to classify subjects in categorical groups, to aid in the diagnosis when used with other additional information, to screen at a high level where no a priori reason exists, to be used as a prognostic marker, to be used as a disease or injury progression marker, to be used as a treatment response marker or even as a treatment monitoring endpoint.

By "electronics module" or "EM" or "reusable electronic module" or "REM" or "multi-functional biosensor" or "MFB" we mean an electronics module or device that can be used to record biological signals from the same subject or multiple subjects at different times. By the same terms, we also mean a disposable electronics module that can be used once and thrown away which may be part of the future as miniaturization becomes more common place and costs of production are reduced. The electronics module can have only one sensing function or a multitude (more than one), where the latter (more than one) is more common. All of these terms are equivalent and do not limit the scope of the invention.

By "biosignals" or "bio signals" or "bio-signals" we mean any direct or indirect biological signal measurement data streams which either directly derives from the human subject under assessment or indirectly derives from the human subject. Non-limiting examples for illustration purposes include EEG brainwave data recorded either directly from the scalp or contactless from the scalp, core temperature, physical motion or balance derived from body worn accelerometers, gyrometers, and magnetic compasses, the acoustic sound from a microphone to capture the voice of the individual, the stream of camera images from a front facing camera, the heart rate, heart rate variability and arterial oxygen from a would pulse oximeter, the skin conductance measured along the skin, the cognitive task information recorded as keyboard strokes, mouse clicks or touch screen events. There are many other biosignals to be recorded as well.

By "Return to Play" we mean similar decisions such as return to duty, return to work, return to learn, return to drive, insurance coverage decision (return to coverge) or any other return to activity based decision that has a different context but is essentially the same question about a human subject trying to return to an earlier state to resume an "activity" that they participated in previously.

A System of Multiple Transducers to Both Stimulate and Record Physiological and Brain Response The systems and methods of the invention comprise multiple transducers to both stimulate and record the physiological response of the brain and the body in order to assess its health and function. Central to the system is the ability to directly record brainwave activity from an electrode place non-invasively on or near the scalp. Moreover, additional information on brain health and function can be derived from transducers that measure position and motion, temperature, cardiovascular properties like heart rate, heart rate variability, and arterial oxygen, as well as cognitive information, speech, eye movement, and surface skin conductance to name a few non-limiting additional biological signal measurement data stream examples. It is often necessary to bring the system to the human subject, getting out of the hospital or doctor's office and enabling data collection in the home or sports field or combat theater, thus providing accessibility to the brain health and function assessment from a lightweight and portable form factor. Moreover, it would be advantageous to have a minimal cost associated with the system so that it can be used around the globe to help those in need of brain health and function assessments.

A solution to these problems includes the creation of a system of body worn or body proximal electronic modules (EMs or REMs) with the ability to both record biological signal measurement data streams as well as present stimuli to the human subject in the form of various sensory and cognitive challenges and tasks. In particular, one such electronic module (EM or REM) can be placed in the vicinity of the head and be either reused over and over if it does not touch the human body or disposed of if it comes in direct contact with the human body.

Figure 1:
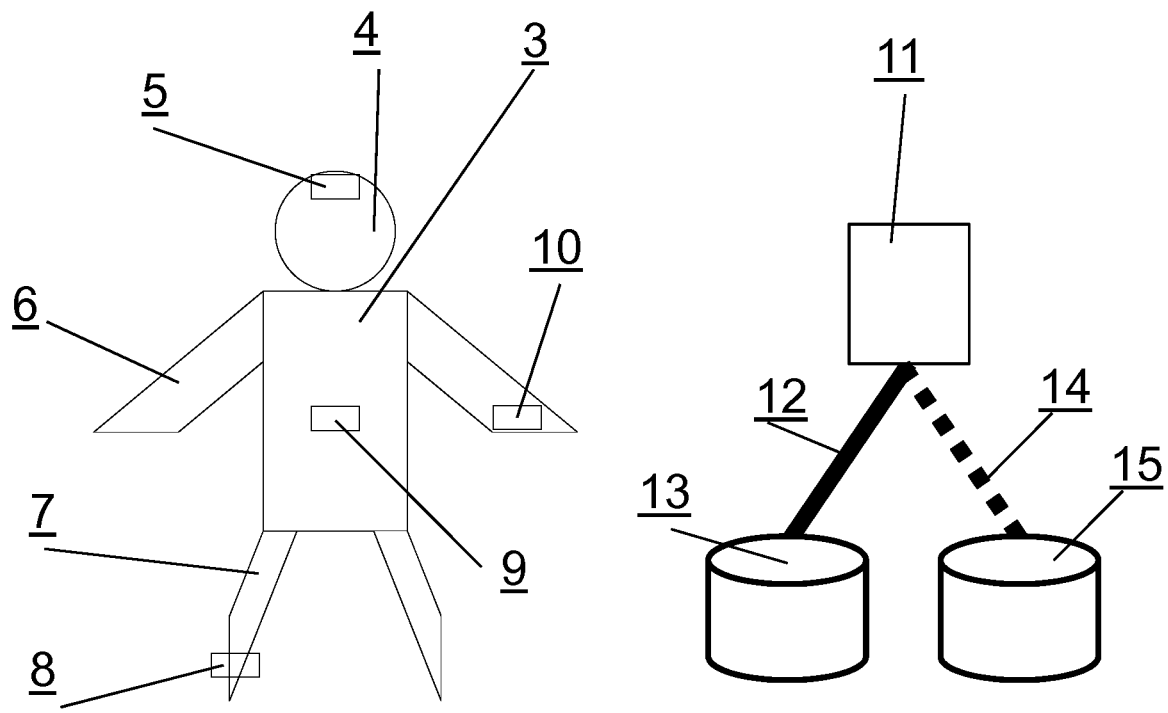
FIG. 1 is a schematic diagram illustrating a human body outfitted with multiple REM modules as well as a nearby peripheral microprocessor (MCU) with direct or wireless access to electronic medical records.

In one embodiment of the system, as illustrated in FIG. 1, a human subject 3 is outfitted on their head 4 with an electronic module or reusable electronic module (REM) 5, which has several sensors and transducers within it to both stimulate the human subject and record biological signal measurement data streams ("bio signals") in a precise fashion driven via software either embedded within the REM on a local microprocessor control unit (MCU) or running on a nearby peripheral MCU. In this system, limb 6 in the form of an arm or limb 7 in the form of a leg can hold additional REM modules 8 or 10 for additional readout and acquisition of additional biological signals. As desired, an REM module 9 is placed on the trunk of the human subject or up by the chest or around the neck. Nearby or connected via wireless interface, a peripheral MCU 11 would both control the standardized application of sensory and cognitive stimuli as well as coordinate the extensive data acquisition of the biological signals derived from the human subject. One could envision that the peripheral MCU 11 as either a laptop, tablet PC or smartphone of today, or perhaps it may be sitting in separate location altogether from where a human subject is immersed in an audio-video like home theater of image, sound, and other sensory stimuli. It is contemplated that the REM modules could eventually interface with each other via newer RF technology which enables long distance communication with large bandwidth. Importantly, peripheral MCU 11 may have database access either locally via a hard wire 12 to a mass storage device like a hard drive 13 or, alternatively, it may be connected via a wired or wireless network interface 14 (e.g. ethernet cable, Wi-Fi, cellular data modem, satellite data modem to name a few non-limiting examples) to a remote mass storage device 15 with remote MCU capability. The purpose of the access to a database is to enable the system of the present invention to access and pull down additional information about a human subject from electronic records that may exist in some other location and where either downloaded locally to the peripheral MCU 11 or available remotely through network connectivity 14 to remote data base 15 (for instance to pull genetic information or other lab results into the system to make predictive signatures more accurate or precise with the inclusion of blood type, last recorded blood pressure, or ApoE genotype status as non-limiting examples). In either case, once a unique patient identification number has been entered and proper security clearance made (such as two factor authentication), then many additional variables of data can be pulled out of the data base records stored on mass storage device 13 and/or 15.

Figure 2:
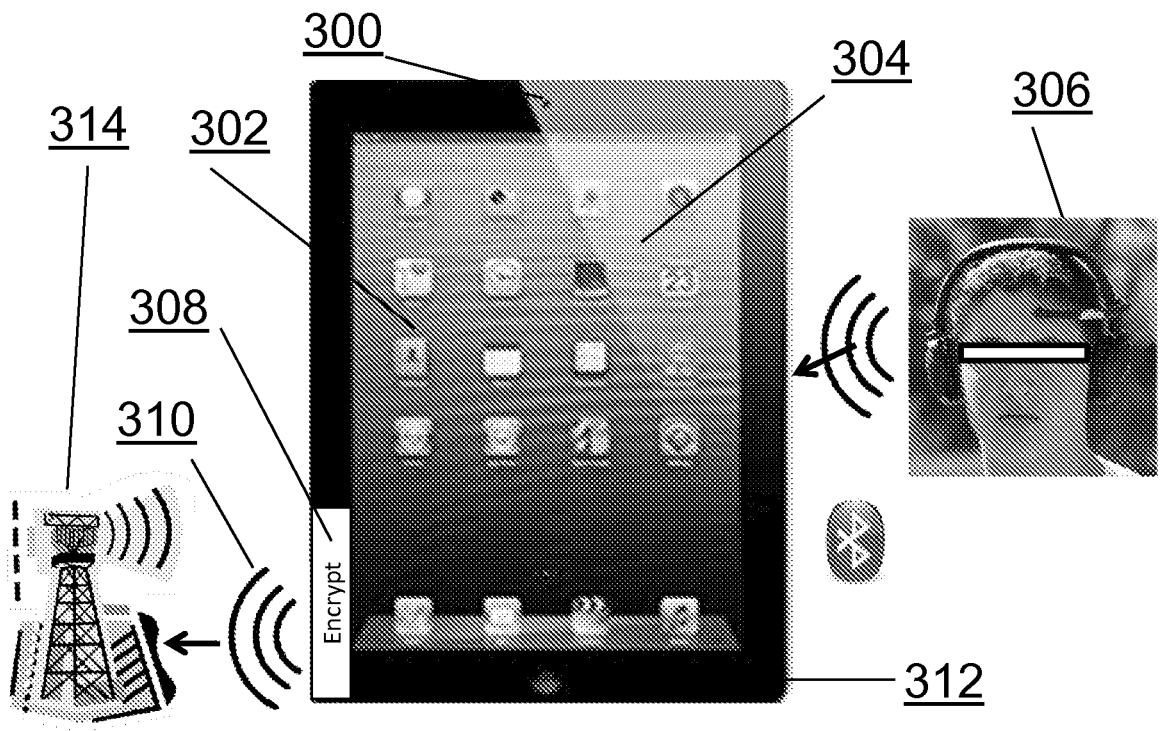
FIG. 2 is a schematic diagram illustrating the flow of data from the human subject wearing headset to the laptop, tablet or smartphone where it is encrypted and transmitted to the cloud.

Another embodiment of the invention includes a data recording and analysis system that includes at least one REM placed on the head of a human subject to record brain related biological health signals, a peripheral MCU, and a cloud based enterprise information technology infrastructure to process and report the data that has been collected. In particular, FIG. 2 illustrates an electronic REM module 306 on a subject's head transmitting wireless data to peripheral MCU (in the form of a tablet PC) 304. While the data is being collected through the Bluetooth port in the MCU, the camera 300 is recording a movie of images of the subject as they perform tasks to not only verify their identity but also to analyze their eye and facial movement for features of interest (including saccade). Microphone 312 records the voice of the subject for voice recognition analysis, while built-in accelerometer and gyrometer 302 measure the stability or lack thereof of the subject, while touch screen 304 of the peripheral MCU records events at precise times and spatial (x,y) locations on the touch screen. Finally, when all the various data streams are complete, along with demographic and personal health information, the entire package of information is encrypted locally using AES-128 or AES-256 bit encryption (or equivalent security measures) 308 before being transmitted at 310 to the virtual or remote based servers through an internet connection 314 which could be Wi-Fi, Ethernet, cellular or satellite in nature.

Figure 3:
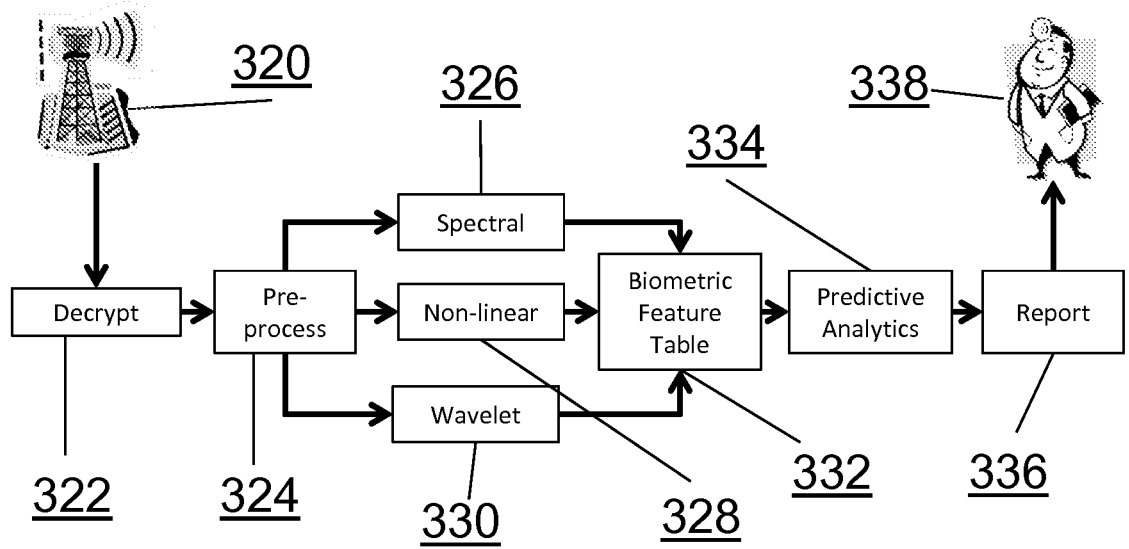
FIG. 3 is a schematic diagram illustrating the arrival of the encrypted data package where it is decrypted, passed through signal pre-processing for artifact detection, then through various signal processing modules for biometric feature table assembly and predictive analytics.

Once the data is received by the virtual server 320 connections, as shown in FIG. 3, it is decrypted by appropriate algorithms with the key 322 and then sent on for pre-processing to identify areas of artifact such as eye blink, drop outs, saturated rails, movement artifacts, EKG artifacts or other known artifacts at 324 as described in U.S. Provisional Patent Application No. 61/773,428, filed Mar. 6, 2013. Once the artifacts have been identified and characterized, the regions of good data for each of the various data streams are passed through signal processing software to extract candidate features from each of the data streams available. In particular, a spectral analysis or FFT module 326 is applied to the data signals, a non-linear dynamics module 328 is applied, as is a wavelet transform module 330. Once each module has extracted the relevant and candidate features from each block of data, the software then assembles an extracted biometric feature table 332 including each of the candidate features from each of the streams of data, including a listing of the artifact features as possible diagnostic features as well. From the biometric feature table 332, predictive analytics 334 are run on the unknown subject and the predictive models generate an output by either classifying the subject into one of several groups or classes or alternatively predicts a regression score as an output. These information are then compared to either baseline/earlier data from that same subject or from a demographically match population's normative data and a report 336 is generated. The report 336 is then sent electronically to physician 338 who is able to remotely interpret the report and provide their interpretation before the report is sent back to the point of care for action by the healthcare provider who captured the data in the first place.

It should be pointed out that the artifacts detected in the pre-processing module could be used themselves as candidate features to help classify or regress unknown human subject information according to a verified and validated multi-variate predictive statistical model as described in U.S. Provisional Patent Application No. 61/773,428, the disclosure of which is hereby incorporated herein in its entirety.

Figure 4:
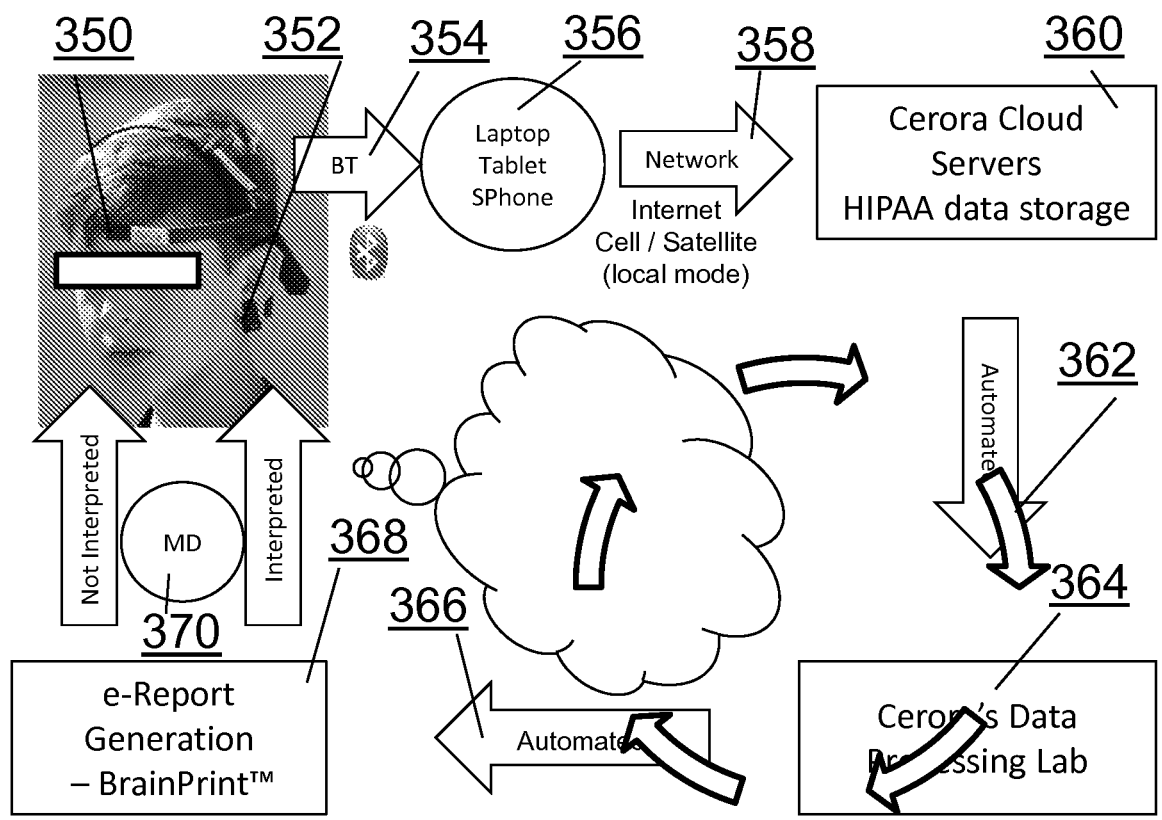
FIG. 4 is a schematic illustration of the diagnostics as a service system.

An alternate view is provided by FIG. 4 where active sensor remote electronic module (REM) 350 is mounted with ear clip 352 on the human subject's head. The Bluetooth or other local means of connectivity 354 transfers the data to the peripheral MCU 356 (laptop, tablet or smartphone) whereby the data is encrypted and sent to the network 358 via internet, cellular or satellite connectivity. Once at the virtual and remote servers 360, the data is automatically decrypted and processed 362 at the data processing center 364 remotely. Once pre-processing, signal analysis, and predictive modeling are complete, the system automatically 366 generates a report 368. This report is then sent back to the point of care if requested by an appropriate physician 370 or to an appropriate physician 370 for interpretation before being sent back to the point of care to insure that a physician remains a part of the diagnostic cycle.

Figure 5:
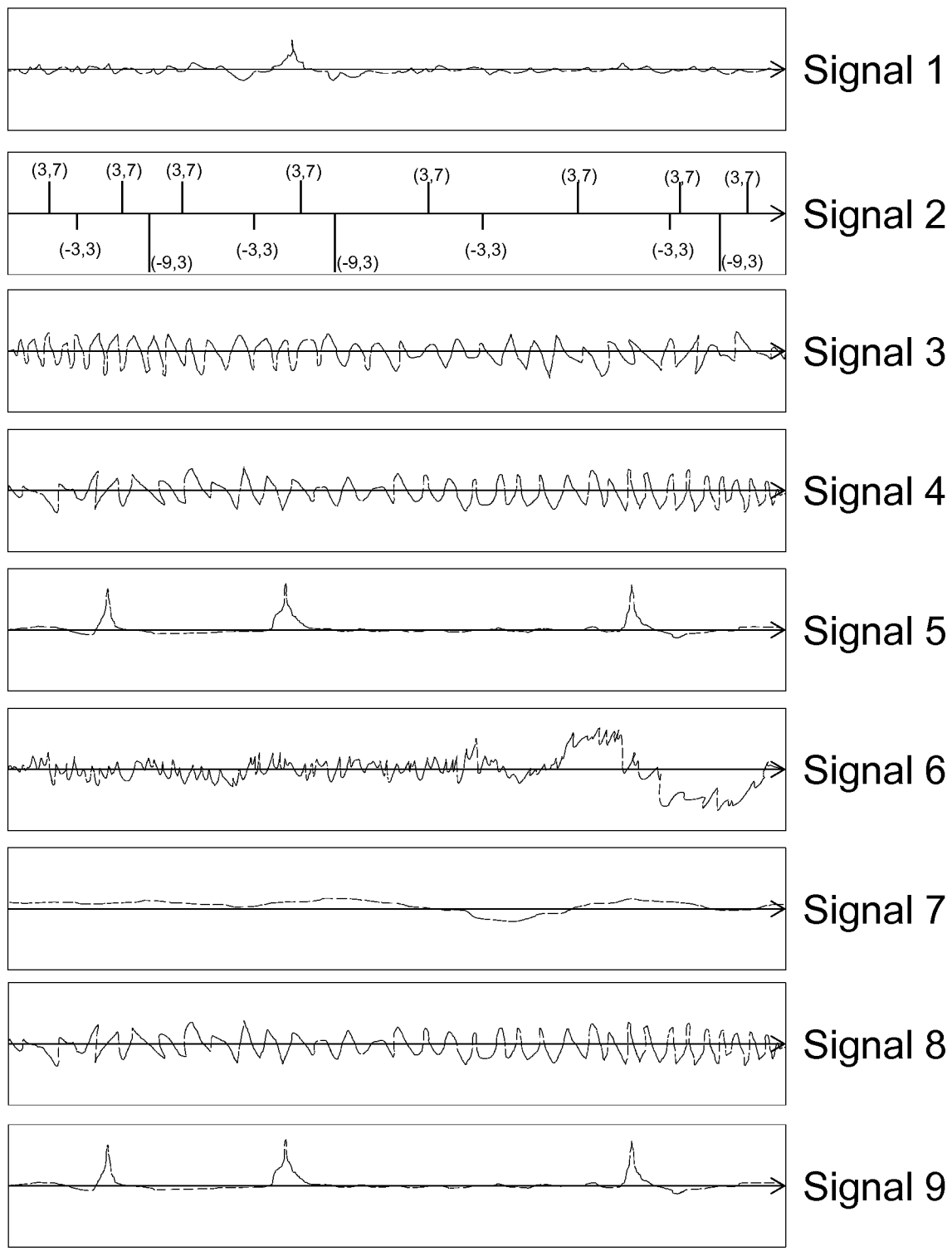
FIG. 5 is a schematic illustration of a series of nine different bio signals from a multi-modal stimulation and data acquisition system.
Figure 6:
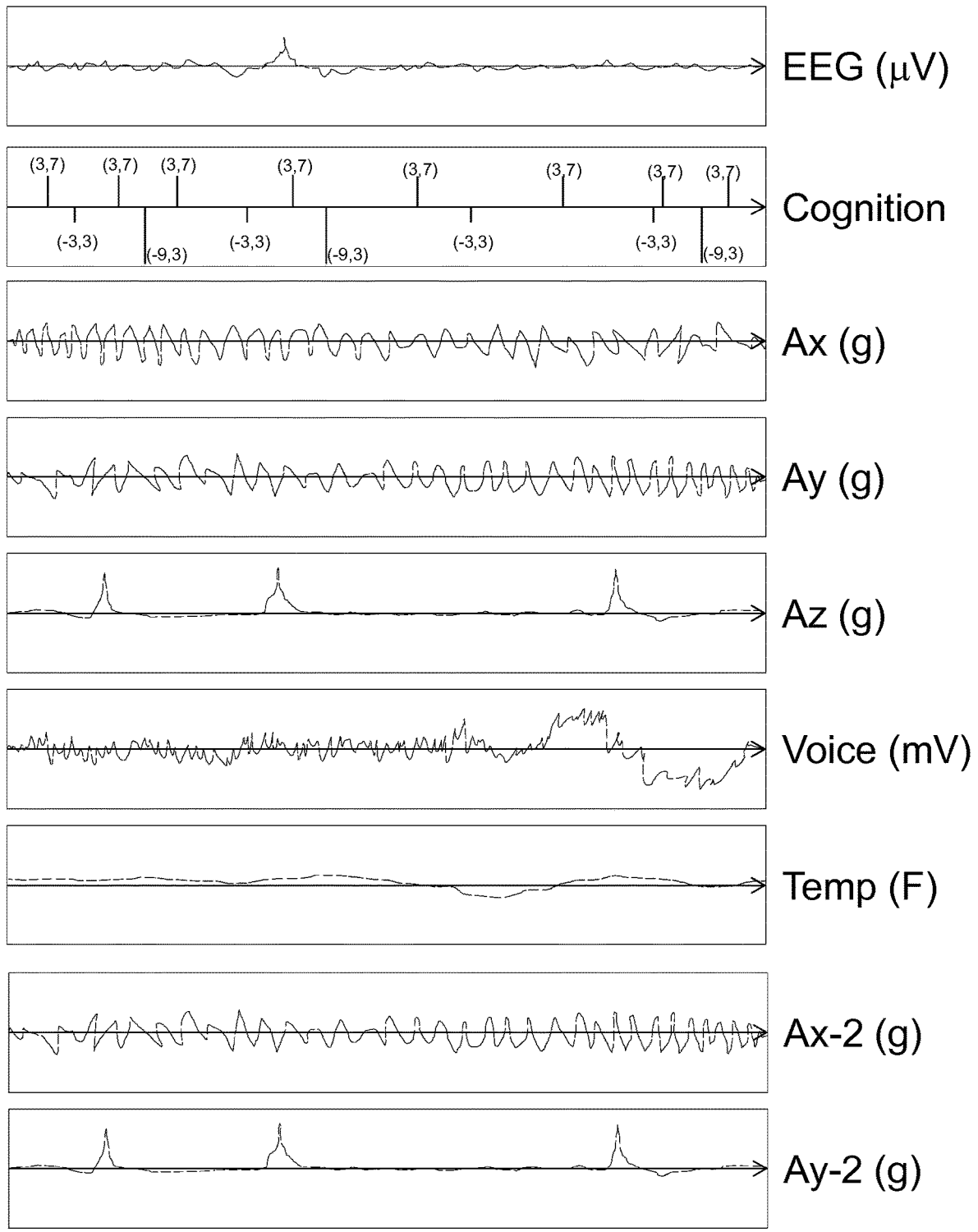
FIG. 6 is a schematic illustration of a series of nine different biological signals from a multi-modal stimulation and data acquisition system. (Note: synthetic data, not from real human subjects).

If one examines closely the output from the various sensors and transducers place on or nearby the human subject, one can see the quantitative output from each sensor or transducer, after analog to digital conversion by an ADC into a discrete flow of digital information. FIG. 5 schematically illustrates the output from nine sensors and transducers (artificial data created for illustration purposes only), each labeled as signal 1 through signal 9. This illustration does not include data from other biological signal measurement data streams such as the forward facing image camera, a pulse oximetry, skin conductance electro-dermal measurements, as a few non-limiting examples of what is not included. In FIG. 6, each of the generic sensor labels has been replaced with an example bio signal stream (with the same artificial data created for illustration purposes only). From the top of the FIG. 6, one sees the electroencephalogram or EEG in micro-volts ($\mu V$) plotted on the y-axis as a function of time t along the x-axis. In the second trace down, neuropsychological cognitive data is illustrated in a plot where discrete response "events" to computer neuropsychological testing are being captured as key strokes on a keyboard, mouse clicks with a position (x,y) on the video monitor's screen or alternatively on a touch screen display as touch "events" where the location (x,y) much like a mouse click is recorded as (x,y) spatial pairs at a given time t (x,y,t). In the next three traces (third, fourth and fifth from the top) one sees three independent traces from a 3-axis digital accelerometer or a 3-axis analog accelerometer after passing through an ADC labelled Ax (g), Ay (g), and Az(g). Acceleration is often expressed as a fraction or multiple of the gravitational constant acceleration g=9.8 meters/second. In the sixth trace from the top (or fourth from the bottom), one can see a microphone recording trace labelled Voice (mV), typically sampled at either 1 or 2 bytes per sample and from 5 ksam/sec or 8 ksam/sec or 12 or 16 ksam/sec, although many other sampling frequencies are possible. In the third trace from the bottom labelled Temp(F), the temperature of the human subject is plotted across time to investigate if any of the sensory stimulations or cognitive tasks are having an effect on core body temperature. Lastly, the bottom two traces exemplify two of three axes of accelerometer data from a second REM labelled Ax-2 (g) and Ay-2 (g), perhaps located on the trunk at the chest or small of the back, or on a limb around the wrist or perhaps ankle. If well registered in time, the multiple streams of biological signals enable several clever and interesting techniques of data acquisition and analysis.

Simplified Form Factor for the Acquisition of a Multiple Streams of Biological Signal Data in the Assessment of Brain Health and Function The systems and methods of the invention comprise device and equipment form factors that can easily be positioned on the human body to both stimulate various senses as well as collect a multitude of bio-signals, can be re-used in part and disposed in part, and utilized locally using personalized and disposable materials when they touch the human body. It is often necessary to insure the integrity and sterility of any item that comes in contact with a human test subject by either disinfecting the applied part or dispensing of the previous one and using a fresh and unused sterile set of materials that come in contact with the human subject. Moreover, it would be advantageous to have a minimal cost associated with the disposable parts that get thrown out as waste into a trash can.

A solution to these problems includes the creation of one or more electronic modules ("EM") or reusable electronic modules ("REM") or multi-functional biosensors (MFB) that can be placed on the body to record bio-signals from the body. In particular, one such EM module can be placed in the vicinity of the head and be either reused over and over if it does not touch the human body or disposed of if it comes in direct contact with the human body.

Figure 7:
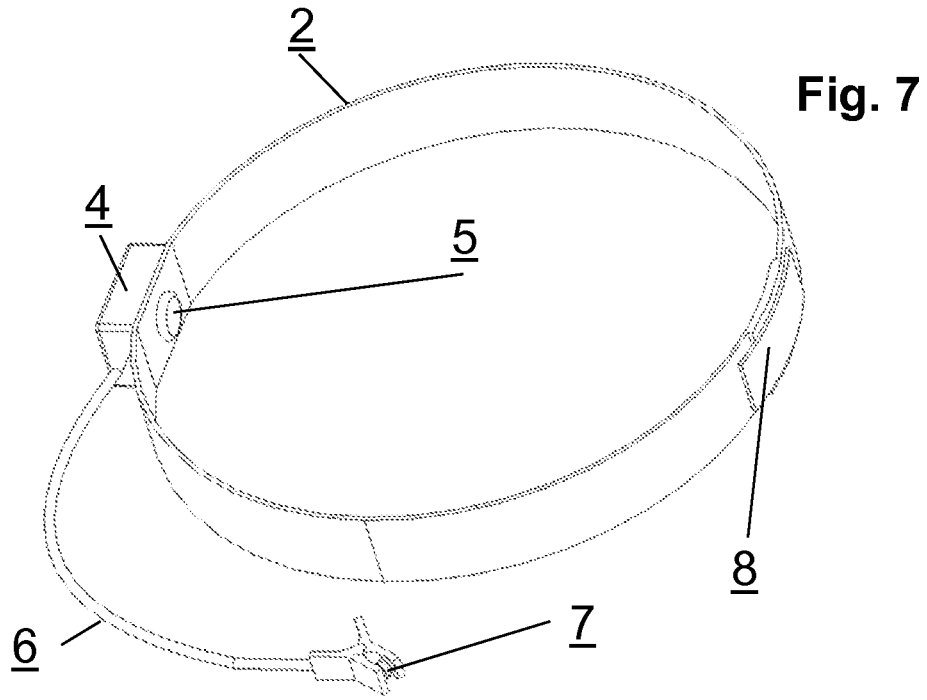
FIG. 7 is a schematic illustration of a one channel regulatory compliant device.

In one embodiment as illustrated in FIG. 7, a form factor of the invention includes a headband 2, which supports an electronic module or reusable electronic module (REM) 4, which has an active brainwave sensor 5 that sits directly on the forehead. The differential input signal is contacted to a non-skull portion of the body, preferably someplace easy to access like the earlobe or top of the ear off of the skull through cable 6 to ear clip 7 which includes either one conductor or two conductors, one for Reference (REF) and the other for Ground (GND). Alternate off the skull locations include the neck as mastoid and the nose, in the vicinity away from the facial skin. The REM 4 and the active brainwave sensor 5 can be attached through a common medical device electronic snap or other simple press electro-mechanical connection. The REM 4 and cable 6 can be attached to the headband 2 via Velcro hook/ladder press closure as well. At the back of the headband, a piece of Velcro or similar press fit closure 8 can be used to secure the headband to the human subject's head with a secure but comfortable tight mechanical fit. In an exemplary embodiment, the head band 2 is made from Fabrifoam's unique fabric-foam dual layer material which stretch easily and is very comfortable to sit on the skin because of their special proprietary water permeation properties of the material.

Figure 8:
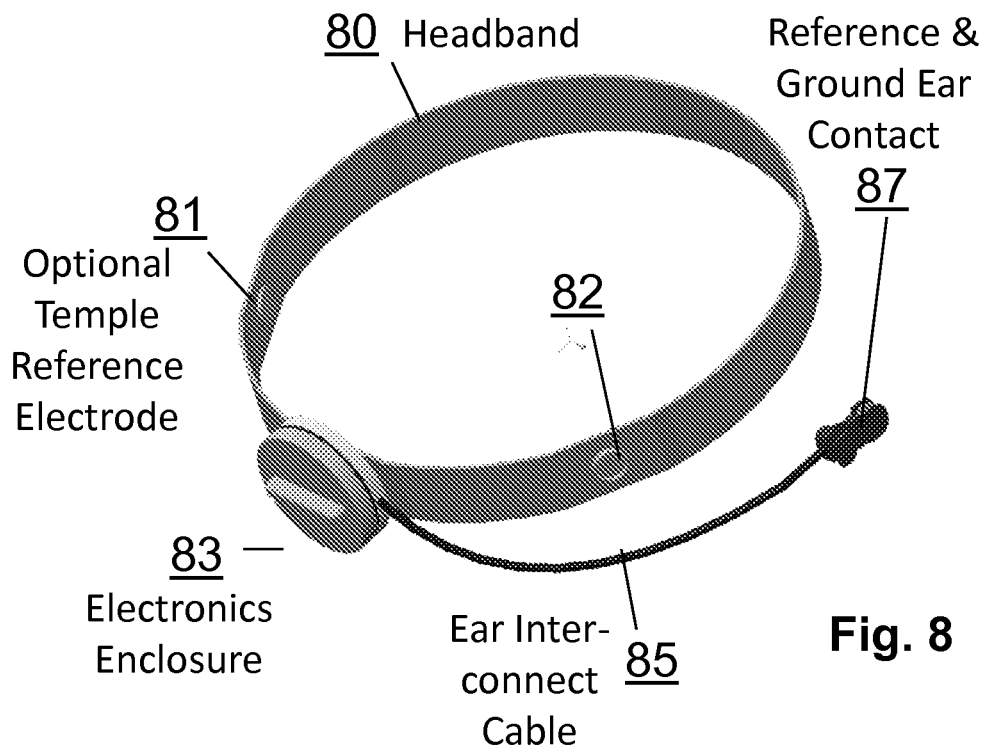
FIG. 8 is a schematic illustration of a headband with alternate electrode placements at each temple.

In another alternate embodiment, shown in FIG. 8, headband 80 has REM 83 attached as before but now there are additional electrodes such as on the temple 81 and or otherwise located around the head at position 82 and attached to the headband 80. In this embodiment, two, three or four channels of EEG data can be recorded to monitor both hemispheres of the brain as well as other spatial locations. Interconnect cable 85 and ear clip 87 for REF and GND ear contact are as described before.

FIG. 9 provides a series of alternative electrode configurations. FIG. 9A provides a pair of views of alternate electrode configurations whereby the normally circular electrode is divided in two hemi-circles or alternatively whereby a normally square or rectangular electrode is divided in squares or rectangles. FIG. 9B provides a view of an alternate electrode configuration whereby the whole conductive electrode has been sub-divided into 3 equal conductive parts separated by insulator, either starting from a circle into 120 degree arcs as in FIG. 9A upper or a rectangle into equal squares FIG. 9B lower. FIG. 9C provides a view of an alternate electrode configuration whereby the normally circular (upper) or square electrode (lower) is divided into 4 equal conducting electrodes depending on geometry and again divided by insulators to make 4 independent electrodes within the existing form factor. For instance as a non-limiting example, a circular electrode divided into four would look like the four quadrants of FIG. 9C upper, while that of a square divided into four would look like the array of conducting electrodes shown in FIG. 9C lower. Thus, if one were to use two independent electrode clusters, each divided according to one of the illustrations shown in FIG. 9, then one would be able to deploy a 4 channel (2 locations with 2 electrodes at each location), a 6 channel (2 locations with 3 electrodes at each location) or an 8 channel (2 locations with 4 electrodes at each location) data acquisition system in the same physical space easily accessible along the area of the skull under the REM module's support headband with good mechanical and electrical connectivity.

Trunk Electronic Modules Gather Trunk Data in Addition to the Head Based REM

One aspect of the present invention includes the use of additional electronic modules to collect trunk data, either located in vicinity of the small of the back, around the chest, or on the neck, at the same time that the head REM is collecting brain/skull related biological signal data. For instance, while a human subject is undergoing a vestibular or balanced based assessment during a concussion battery of tests, the human subject could be asked to stand on a firm surface in various postures, consistent with the Balanced Error Scoring System or BESS (Guskiewicz et al). Rather than have an athletic trainer or manager subjectively score and evaluate the human subject for various subjective errors, as is presently done, a multi-axis accelerometer can measure objective biological signals of the human subject's stability based on their head movement and motion while conducting the task and while the EEG sensor is collecting contemporaneous brainwave data.

Similarly, accelerometer and/or other position/motion sensors placed along the trunk, spatially from the neck, to the chest, to the small of the back enables further objective measurement of body motion from which to further assess the human subject's ability to react to change when asked to stand on an elastic or unstable surface while accelerometers and gyrometers in the head REM continue to measure brainwaves and head stability during the task.

In one embodiment, additional accelerometer data is collected by a trunk REM attached to the waist or small of the back while a third REM, attached near the chest or neck, further quantifies the human subject's balance skills simply, quantitatively and inexpensively using a 3, 6 or 9 degree of freedom system at each physical location (head, neck/chest, waist/back). In addition to conducting these balance related tasks on a firm surface, use of an inflatable and disposable pillow or air cushion made from strong plastic provides an inexpensive means to assess the human subject on a pristine and unused soft and unstable elastic surface suitable for medical device use. When reusable foam cushions are permissible, like the Airex model cushion recommended in the BESS instructions, they are excellent second surfaces for A versus B comparisons. In instances where repeated use by multiple human subjects is not permitted, such as in medical evaluations and assessments, the use of a compact, disposable, and inexpensive elastic and unstable inflatable pillow device for a human subject to stand on could advantageously assist in a concussion or other balance/vestibular system assessment and is a part of the invention. Here, the same A versus B comparison is possible, but with the added benefit of a single use disposable unstable surface, such as the inflatable air pillow.

Incorporation of a Microphone and/or Camera in an REM Module

In one embodiment, additional data transducers are built into the REM module such that the system can acquire diverse streams of bio signal data. One particular embodiment includes the inclusion of either an acoustic microphone coupled to an analog to digital converter or the use of a digital microphone which has essentially the same functionality, just engineered into a single package for ease of integration into the REM electronics. Typical digital outputs are in common standards such as RS-232, UART, SPI, and I2C for local area serial digital communication. An advantage of the present embodiment is that the control of timing by the local embedded MCU in the REM is typically tighter and more precise (sub milliseconds with the ability to approach micro-second timing precision if not go beyond to sub-microsecond timing precision) than can typically be achieved with the peripheral MCU, such as an Apple iPad or Android tablet or Windows Laptop unless one attempts to run a special "real-time" implementation of those operating systems, some of which do not yet exist (e.g Apple iOS does not yet have a real-time OS that the programmer can program control over).

In FIG. 10, one can see a rendering of a head based REM module which is powered by an AAA battery. In the alternative, it could be powered by coin style batteries for a slimmer and more compact profile. In addition to a standard "power/pairing" switch 92 and power/pairing indicator LED 94, one can see the incorporation of an acoustic microphone 96 into the REM design as well as a forward facing digital image sensor 98 (essentially a movie camera). The microphone 96 is then capable of picking up those sounds in the immediate area of the human subject including the speech of the scan administrator, the speech of the software narrator, and their own speech (the subject taking the scan), as non-limiting examples of sounds that would be captured by microphone 96. Moreover, coughs, sneezes, laughs, falls, etc. would also be captured in real-time with a tight precision as managed in hardware by the embedded MCU in a real-time data acquisition environment.

The image sensor 98 would be capable of acquiring video rates or faster of image data. The view of the images would depend on where the REM is placed on the head and the orientation of the subject's head. The use of the video images could enable tracking of the eye at the sample or refresh rate of the sensor, typically 30 frames per second or 60 fields per second of a standard interlaced NTSC video device. That said, spatial sub-sampling of a sub-region of interest of a CCD pixel array can greatly accelerate the full frame or field rate to enable 60, 80 even 100 Hz sample rate of a smaller field of view which could advantageously be focused on the eyes for the analysis of saccade to distractions or other neuropsychological tests which have been published within the scientific literature extensively. Of course, either microphone 96 or image sensor 98 could be utilized alone or in combination in various REM modules, depending on the particular circumstances.

Use of Google Goggles or Other Eye Tracking Devices to Monitor Eye Movement

In a recent advance, Google has come out with an eyeglass-like device which can project images and track the eye to move a camera to where one is looking. This sort of technology could be incorporated into an REM or the electronics of the REM could be incorporated into a Google Glass like device to combine the eye tracking capability with the other biological sensor data streams. This could be especially useful when one wants to assess the quality of the neuro opthalmologic tracking of the eye by the brain. Visual Saccade as designed into the Peirce test, King-Devick test, Developmental Eye Movement test, or oddball or mismatch saccade tests are well known to provide meaningful streams of eye gaze information. This system would not compete with high end 128 or 256 sam/sec systems built into goggles and other form factors that are dedicated to this task, rather this would represent one more bio signal data stream that could be analyzed alone and then in conjunction with the other data streams.

Figure 11:
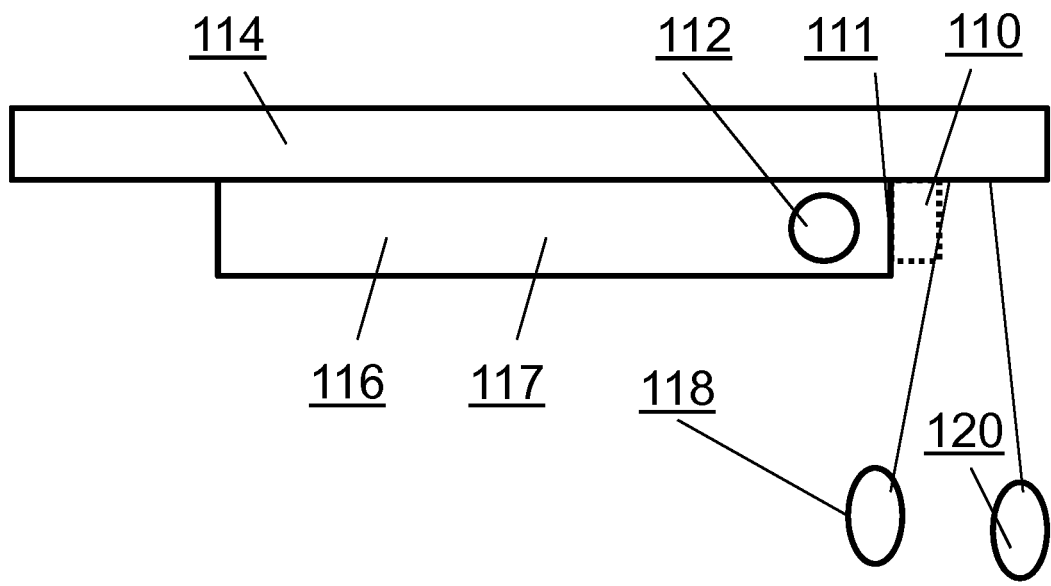
FIG. 11 is a schematic illustration of a Google Glass like device with infra-red eye tracking capability.

In FIG. 11, one can see a block rendering of a side shot of the Google Glass device. Surround member 114 is essentially the piece which wraps around the head from ear to ear and from which all other pieces are supported. The pair of nose pads 118 and 120 supports the device on the bridge of the nose much like eye glasses. Electronics module 116 hangs below and encloses video camera 112 and 9-axis Motion Sensing Unit 117 (Invensense 9650 which includes a 3 axis accelerometer, 3 axis gyrometer and 3 axis electronic compass). The Glass screen and possible eye track reflector/sensor 110 (drawn with dotted lines not solid since transparent in real life) sits to the right in the field of view. The Eye tracking sensor or system 111 within the Glass device could be used in the present invention as one more element of a biosensor data stream, to monitor the position of the eye or eyes, especially during neuro ophthalmologic saccade based visual tasks such as the Pierrce Saccade, King-Devick Test, Developmental Eye Movement (DEM) or proprietary improvements thereof.

The Motion Sensing Unit MSU 117 integrated into the Glass could be used in the present invention as one more element of a biosensor data stream, in particular when one is conducting static balance tasks, such as the various postures of the BESS, or dynamic balance tasks, such as the "stand, walk and turn" task. These additional biosensors would need to be integrated into the overall multi-modal system by streaming data via wired or wireless connectivity to an MCU either embedded into an REM as described elsewhere herein, or alternatively, the electronics module 116 of FIG. 11 could house the electronics for the head REM, serving as the MCU with attachable electrodes placed on the forehead with adhesive to record the brainwave EEG bio signal data stream. Bluetooth, ANT, Zigbee, WiFi are all local area wireless connectivity options, as well as direct wire options using miniature connectors such as USB micro or smaller.

It is also contemplated that the data may reside on a removable SD card in an electronics system or REM and not be transmitted wirelessly, but rather stored locally to a removable mass storage device like an SD card. This alternative has the advantage of not requiring wireless connectivity but gives up the ability to monitor in real time the data streams and the synchronization from interaction with the stimuli. Each "Use Case" is often different so it may be advantageous to have local SD card storage in some instances and not in others. In one non-limiting example, it may be advantageous to have local storage if one wants to monitor a patient for possible seizures over a 24 to 48 hour period of ambulatory biosensor monitoring. Thus in this strictly passive monitoring application, stimulation or probe presentation is not as important, so use of a peripheral MCU like a tablet or smartphone may not be necessary.

Embodiments Around Activated Patient Sensory and Cognitive Stimulation

Application of sensory stimulants to the patient allows more focused and detailed evaluation of multiple modes of biological signal data streams. Multi-modal data can be acquired by measuring EEG signals at the same time that accelerometer based signals, temperature signals, pulse oximetry signals, eye gaze signals and other biological signals are being simultaneously acquired before, during and/or after a patent's response to a sensory stimulant or cognitive challenge.

Photic Stimulation

Visual stimulants such as photic stimulation while a subject's eyes are closed or via the presentation of certain types of affective photographic images can be utilized either independently or via the data capture microprocessor device (MCU) (computer, tablet PC, cell phone, or other dedicated custom device with microprocessor and wireless connectivity) used to collect the wireless bio-signal data from the various REM units on the head, neck/chest, waist/back, hand/wrist or foot/ankle. In one particular embodiment, the Google Glass display is used to stimulate the right eye with photic stimulation of various spatial and temporal frequency in contrast to the stimulation possible to the asymmetric left eye where no Glass display is located. This asymmetry can be leveraged to conveniently both stimulate and record the brain of the subject from a Google Glass.

Figure 12:
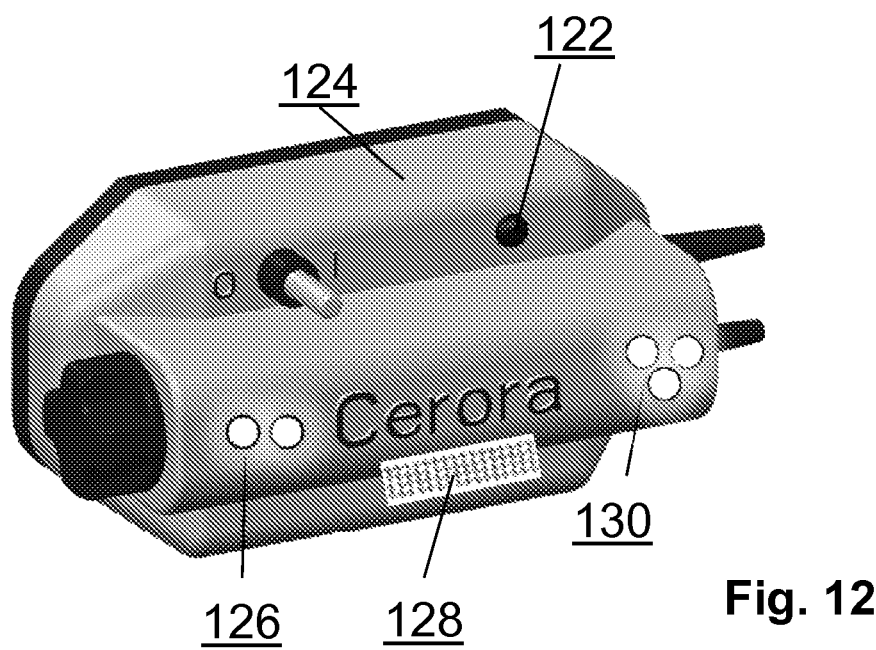
FIG. 12 schematic illustration of a headband supported electronics module with both a dual LED, 3-color montage LED and any array of LED point sources for photic stimulation.
Figure 13:
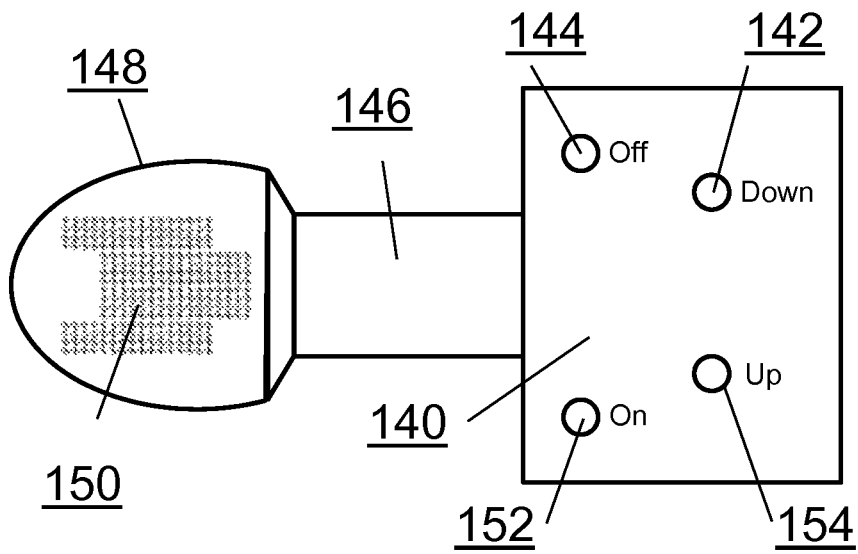
FIG. 13 is a top down schematic view of an electrical tongue stimulator for the brain.

In one particular embodiment of the present invention, as shown in FIG. 12, an isolated LED 122, a pair of LEDs 126, a triple combination of LEDs 130 or an LED array 128 can be mounted on the front of an head REM module 124 and directed forward from the forehead or angled downward slightly so that a mirror or glass surface from a video monitor can reflect the light output from the LED back towards the eyes when they are closed for photic stimulation. The advantage of this sort of approach, over utilizing the video monitor in the peripheral MCU (e.g. laptop, tablet PC, or smartphone), is that the dedicated LED drivers can be housed within the REM which enables orders of magnitude more precise temporal response of the LED(s) than is typically possible from a peripheral MCU operating system (MS Windows, Apple iOS or Google Android). A non-real time OS is generally not be compared to an embedded real-time controller, which exhibit measured jitter in the sub-millisecond range, sometime even the micro-second range, instead of the 10-50 millisecond latency range, typical of Microsoft Windows, Apple's iOS or Google's Android non-real-time operating systems.

Also, by use of three primary color LEDs (a Red, a Green, and a Blue LED), one can make color combinations that slide across nearly all colors of the rainbow spectrum, enabling the choice of color stimulation of the light by mixing appropriately the LED outputs to make the rainbow of colors of the electromagnetic spectrum. Importantly, white light can be created from the superposition of all three wavelengths of light in equal amplitude. This would advantageously enable the embedded software to control the REM MCU via the Bluetooth link and control the LED output with a real-time embedded processor or something with much shorter latency than the Windows, Apple or Google operating systems mentioned above.

Visual Stimulation

In one particular embodiment of the invention, photographic images are presented which have desirable emotional and reactive properties. In one embodiment, the photographic images have been artificially manipulated in software like Adobe Photoshop in an interesting fashion. They are then presented as a sequence of images to assess the mood or emotional response qualities of an individual under assessment. For instance, an image of a pig can be altered so as to add wings and then be superimposed above a wavy ocean surface. In this fashion, the subject under assessment would see a "flying pig" presented which would typically result in a smile from a healthy normal individual as we normally do not see pigs fly. Alternatively, when someone is less affective, displays a mood or emotional dysfunction, imbalance, or disorder, perhaps is suffering from a concussion or mild traumatic brain injury, the subject may not react in the normal or normative manner. This altered reaction to the photographic image can be biologically characterized, measured, monitored and observed through the various biological signal data streams from the various sensors within the head REM module or peripheral REM modules. In particular, use of galvanic skin conductance is an excellent means to assess emotional response as this biosensor measures the skin conductivity which changes when anxiety (in the form of sweat or skin perspiration), fear (again sweat or perspiration) and other emotional states of an individual.

Thus, in this fashion, a sequence of images from a short stack of photos, for instance like N=4 images, to a long stack of photos, like N=30 images, can be presented to a subject with a set frequency (e.g. 0.1 Hz or 0.05 Hz) or time delay between transition of images on the video monitor (e.g. display each for 15 seconds in one instance or for 3 seconds in another instance).

As an alternate embodiment, the International Affective Picture System (IAPS) can be utilized. The International Affective Picture System (IAPS) is being developed to provide a set of normative emotional stimuli for experimental investigations of emotion and attention. The goal is to develop a large set of standardized, emotionally-evocative, internationally-accessible, color photographs that includes contents across a wide range of semantic categories. The IAPS (pronounced eye-aps) is being developed and distributed by the Center for Emotion and Attention (CSEA) at the University of Florida which has already calibrated photograph images with various valences can be utilized to provide a calibrate stimulation from which one can quantitate the characteristics and biometric response of the human subject under assessment. Reference: Lang, P. J., Bradley, M. M., & Cuthbert, B. N. (2008). International affective picture system (IAPS): Affective ratings of pictures and instruction manual. Technical Report A-8. University of Florida, Gainesville, Fla.

Auditory Stimulation

Sensory stimulants such as sound also may be provided either independently or with the sound card within the data capture microprocessor device (MCU) (computer, tablet PC, cell phone, or other dedicated custom device with microprocessor and wireless connectivity) used to collect the wireless bio-signal data from the REM. Sound events are triggered via the speaker or sound card on the computer at various times for the patient to respond to both instructions as well as auditory stimulations of a novel nature as described elsewhere. This may be through the speakers as well as through ear buds or other personalized listening devices.

As an alternate embodiment, the International Affective Digitized Sound system (TADS) can be utilized. The International Affective Digitized Sound system (IADS) provides a set of acoustic emotional stimuli for experimental investigations of emotion and attention. This set of standardized, emotionally-evocative, internationally accessible sound stimuli includes contents across a wide range of semantic categories. The IADS (pronounced "eye-ads") is being developed and distributed by the Center for Emotion and Attention (CSEA) at the University of Florida. The calibrated sounds can be utilized to provide a calibrated stimulation from which one can quantitate the characteristics and biometric response of the human subject under assessment. Reference: Bradley, M. M., & Lang, P. J. (1999). International affective digitized sounds (IADS): Stimuli, instruction manual and affective ratings (Tech. Rep. No. B-2). Gainesville, Fla.: The Center for Research in Psychophysiology, University of Florida.

Gastronomic Stimulation of Taste and the Gastrointestinal Tract

Figure 14:
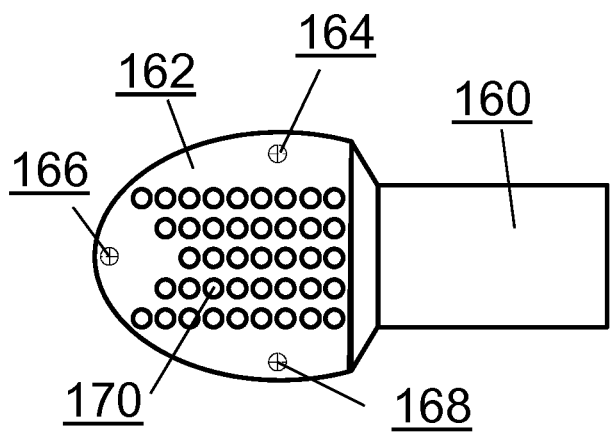
FIG. 14 is a top down schematic magnified view of an electrical tongue stimulator for the brain.
Figure 15:
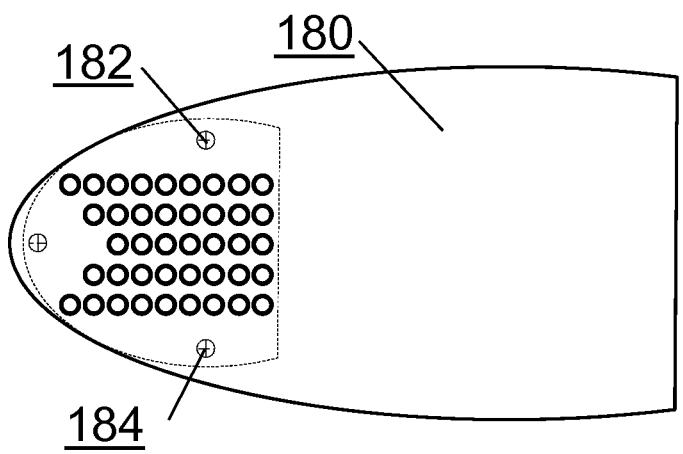
FIG. 15 is a top down schematic magnified view of an electrical tongue stimulator for the brain with the availability of a sterile package via a disposable sheath which enables re-use of the main electrical components.
Figure 16:
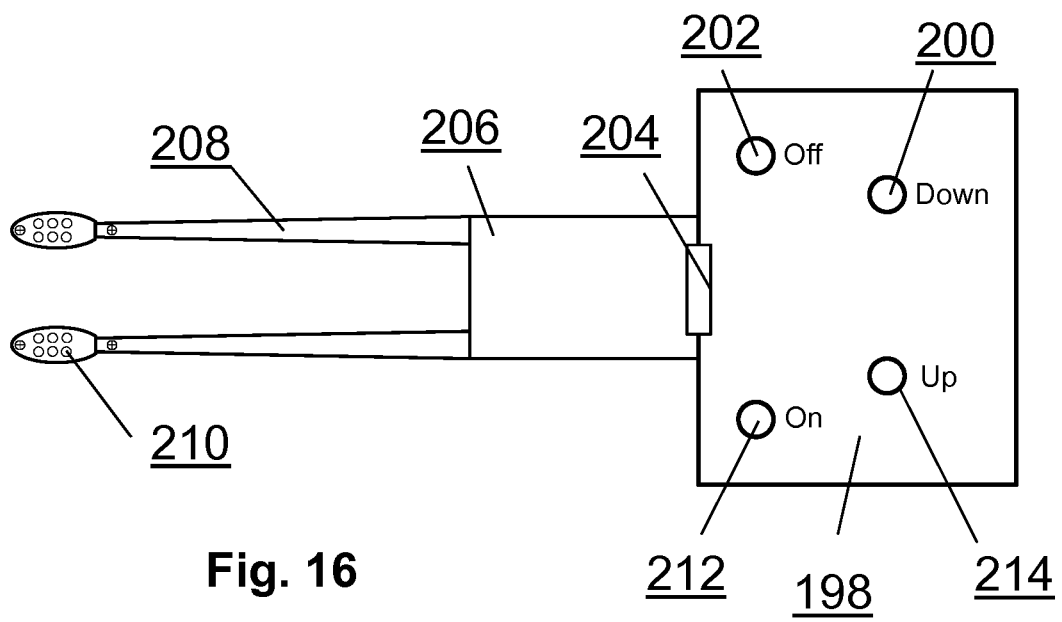
FIG. 16 is a top down schematic view of an electrical nose stimulator for the brain.

In addition to visual and auditory sensory stimulates, gastronomic or tongue based stimulation is also possible with the present invention. In one non-limiting embodiment, shown as FIG. 13, a non-invasive electronic tongue stimulator of the cranial or other nerve is used to activate the brain. The device is powered by a battery within electronics housing 140. Switches enable the device to be turned on at 152 or off at 144 while other buttons increase 154 or decrease 142 the power or intensity of the electronic tongue stimulation. A connecting member 146 transfers signals from the electronics within electronics housing 140 to the mouth piece stimulator 148 that sit directly against the tongue. Electrodes 150 are small concentric circles of electrode designed to directly couple with nerve endings on the tongue. In FIG. 14, one can see a closer view of the tongue activating surface 162 connected structurally and electrically by connecting member 160. The individual electrodes 170 which couple with the tongue directly are drawn as round electrodes with solid lines of insulator. Alignment posts 164, 166, and 168 are used to align disposable conducting plates to transfer charge to the subject but can be thrown away after a single use. FIG. 15 shows such a disposable sheath 180 which includes a matched plate or surface of conducting electrodes. This grid is aligned with the grid on the device by the alignment posts or fixtures 182 and 184 (the third post is not labeled in this figure).

An example real world device like this is called the PoNS Device, developed by the University Wisconsin, Tactile Communication & Neurorehabilitation Laboratory (TCNL)). The PoNS is a battery-powered device and is placed in the mouth where thousands of nerve endings on the tongue can send messages to the healthy areas of the brain. The idea is that the stimulation, in combination with therapeutic exercise, helps the brain form new neural pathways for recovering functions like balance and movement. Those skills are vital for those affected by MS, cerebral palsy, traumatic brain injuries, strokes and Parkinson's disease. In the present invention, the PoNS device can be used to stimulate the brain through the neural response of the tongue, rather than through auditory stimulation, visual stimulation, balance based stability tasks, cognitive tasks as described earlier. The response across the various biological signal measurement data streams can be quantitatively and accurately acquired. Once acquired, the new signals can be analyzed and compared to either earlier measurements within the same subject or to population or other such norms created as reference values. Notice that by use of the PoNS device or other tongue based electrical stimulator designed for brain health assessment, direct assessment of the tongue's neural connections to the brain is possible without the use of food and in a more reproducible and quantitative fashion.

The PoNS device or other tongue based electrical stimulator can be controlled by the peripheral MCU via wireless means with a Bluetooth radio or other RF connectivity means (ZigBee, ANT, Wi-Fi, proprietary) directly or through bi-directional communication with the head REM module which could then subsequently control the PoNS or other electrical tongue stimulator from software embedded within the head REM module's (or any other REM module's) local MCU (such as TI MSP430 16-bit microprocessor or any of the various ARM Cortex M-series microprocessors like the ARM Cortex M3 or M6 or M8). In an implementation where the embedded software in an REM module control's the signaling to the neural tongue stimulator, the precision and timing compared to traditional non-real time operating systems will be considerably better for all the same reasons described earlier.

Olfactory Simulation

A means of olfactory stimulation could be using an UPSIT card or cards from Sensonics where UP SIT stands for the University of Penn Smell Identification Test (UPSIT) to provide olfactory stimulation to the nose of an individual at pre-defined times indicated by the instructions provided by the peripheral MCU software. This could include manually scratching and sniffing each of any number of cards with odors as prescribed and directed. The results are automatically recorded by the various multi-modal biological sensor data streams being generated from the human subject under assessment at that time.

Figure 17:
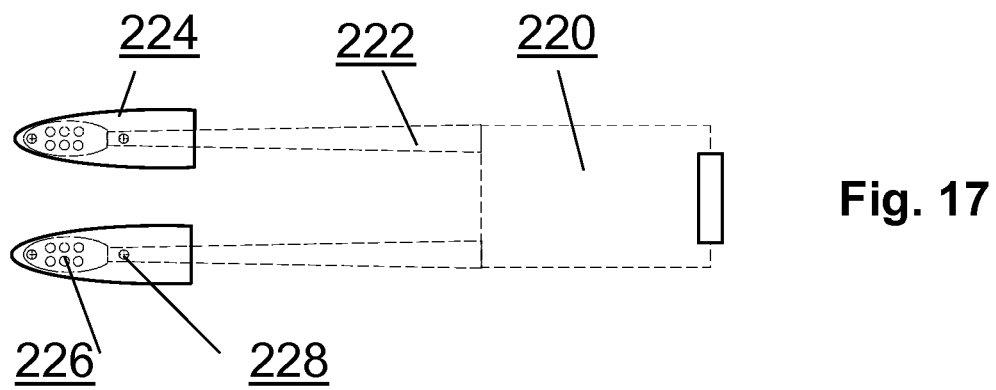
FIG. 17 is a top down schematic view of an electrical nose stimulator for the brain with disposable sheaths to enable re-use of the main electrical components.

In a more automated fashion, olfactory based stimulation is also possible with the present invention. In one non-limiting embodiment, shown as FIG. 16, a non-invasive electronic nose or olfactory bulb stimulator is used to activate the brain. The device is powered by a battery within electronics housing 198. Switches enable the device to be turned on at 212 or off at 202 while other buttons increase 214 or decrease 200 the power or intensity of the electronic nose stimulation. A connecting member 206 transfers signals from the electronics within electronics housing 198 via connector 204 to the thin and flexible nose piece stimulators 208 that sit directly against the receptors of the olfactory bulb. Electrodes 210 are small concentric circles of electrode designed to directly couple with nerve endings on the olfactory bulb. In FIG. 17, one can see a closer view of the nose activating surface 226 connected structurally and electrically by connecting member 220 and nostril support 222. The individual electrodes of 226 which directly couple with the receptors of the olfactory bulb are drawn as round electrodes with solid lines of insulator. Alignment posts 228 are used to align flexible and disposable conducting grids used to transfer charge to the subject but can be incorporated into disposable sheaths 224 (long enough to keep the reusable device away from touching the human subject) which can be thrown away after a single use.

Transcranial Pulsed Current Simulation as a Neuro Diagnostic Procedure

Another embodiment of the present invention is the means of stimulating the brain with cranial stimulation. One such commercial device, the Fisher Wallace Cranial Brain Stimulator provides micro-currents of electricity to aid those with issues of insomnia, anxiety, depression and pain. This device and approach can be used to stimulate the brain and we can measure the response of the brain due to the cranial stimulation. For instance as a non-limiting example, one can scan the subject in a battery of tasks with the system, equipment and methods of the present invention before they receive cranial stimulation from a Carter Wallace or equivalent brain stimulator, and then after the 20 minute therapeutic treatment, the human subject can be re-scanned and the response measured due to the cranial stimulation. Based on this response signature, biomarker differences can be derived for both healthy normal as well as disease, injury, or disorder cohorts. Signatures derived from this dual scan approach can be used diagnostically for any of the various intended uses, as "diagnostically" can mean as many as ten different intended uses as earlier defined.

Particular embodiments of this approach include the use of the cranial stimulator to diagnostically assess for concussion/traumatic brain injury, migraines, mild cognitive impairment and dementias, pre-motor Parkinson's disease, as well as various neuropsychiatric conditions such as depression, bipolar, schizophrenia, anxiety or panic disorder, post-traumatic stress disorder. Additionally, it is contemplated that this approach could have diagnostic utility in the diagnosis of mental disorders of the brain, including multiple personality disorder, dyslexia, hallucinations, phobias, addictions, alcohol abuse, eating disorders such as anorexia or bulemia, obsessive-compulsive disorder, and mood disorders.

Transdermal Pulsed Current Simulation of the Peripheral Nervous System as a Neuro Diagnostic Procedure Furthermore, the present invention contemplates use of transdermal pulsed current stimulation as well, in the form of peripheral stimulation such as TENS units, as this could have an important diagnostic impact on who may have peripheral nervous system issues in addition to diagnosis of central nervous system issues. The results are automatically recorded by the various multi-modal biological sensor data streams being generated from the human subject under assessment at that time.

In one particular embodiment of the invention, a TENS unit is attached to the left and right finger pads which are known to have a lot of nerve endings and stimulated in a characteristic fashion. Brain related response, synchronized to the peripheral stimulation, in the form of an EEG brainwave sensor, galvanic skin conductance, pulse oximetry, cerebral blood flow, temperature and other biosignal data streams would be collected. If the TENS stimulation had cyclic activity in time, then a locked-in signal could be investigated and look for phase lag between the peripheral TENS stimulus and the biosensor responses.

Use of the Multi-Modal System to Create Multi-Modal Signatures for Disease or Injury Using the system of the invention, one can build extracted biometric tables that include features extracted from multiple modes of biological signal data. As a non-limiting example, two groups of subjects, group A who experienced a concussion (mTBI) or mild traumatic brain injury, and group B who did not and serve as Controls (CTL), were recruited under the supervision of an Institutional Review Board. Participants from both groups A and B were scanned identically with an electronic REM module including a single electrode EEG. A 5 minute protocol was implemented including 30 seconds Eyes Closed, 30 seconds Eyes Open, conducting the King-Devick test for approximately 3 minutes and then 30 seconds Eyes Closed, 30 seconds Eyes Open again. The stop watch times and errors for each card of the King-Devick test were recorded manually by the test administrator while the peripheral MCU (a laptop computer) presented the cards and recorded the responses of the individuals via the microphone. The data was blinded to participant for the purposes of artifact detection, signal processing and feature extraction. The extracted feature data table was then quality controlled and scrubbed to remove as many errors as possible. The total time for the King-Devick test was created as one extracted variable and underwent a logistic classification model. The result of this model indicated that the King-Devick time alone predicted the classification of the individuals approximately 62% of the time. Independently, the relative power in each of the delta, theta, alpha, beta and gamma bands was analyzed in a logistic classification model where the EEG feature was the predictor x-variable and the clinical outcome (grp A or B) was the outcome or dependent y-variable in the predictive analytic model. The analysis was conducted in JMP Pro v10 from SAS (Cary, N.C.).

Figure 18:
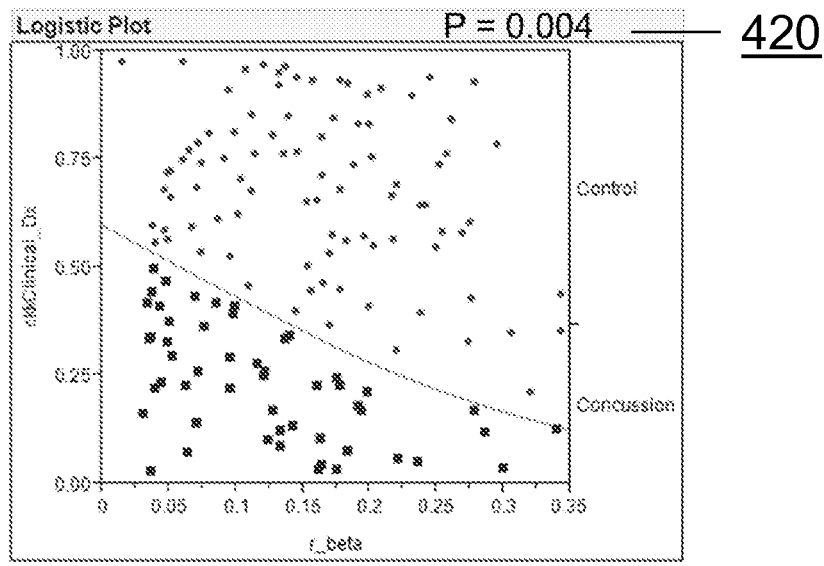
FIG. 18 is a pair of graphical displays of a logistic plot and its corresponding Receiver Operating Characteristic curve (ROC) of an EEG feature (relative beta) used to predict the clinical diagnosis of concussion subjects versus control subjects.
Figure 18:
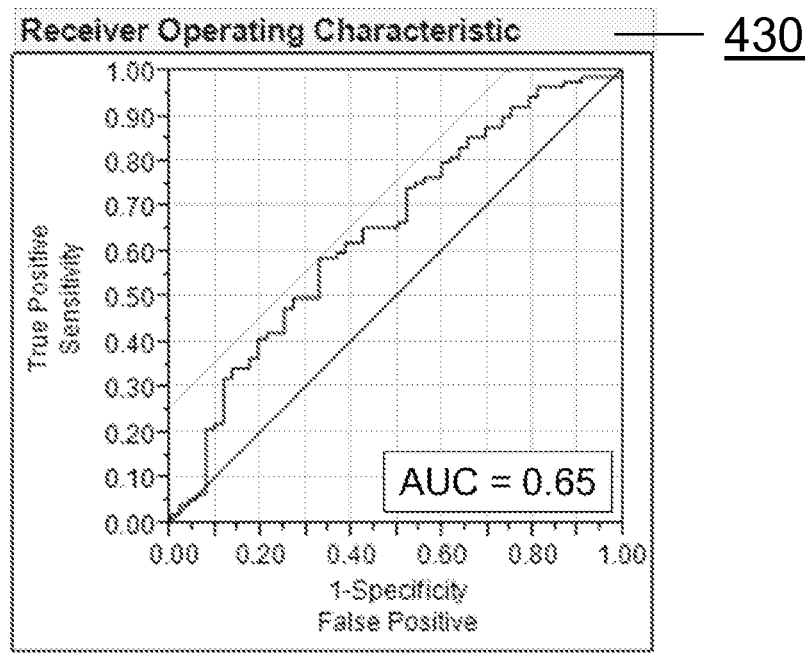

FIG. 18 illustrates the logistic plot 420 for the relative-beta power (from 12-30 Hz) showing a decreased relative beta power in the concussed group A relative to control group B. When one constructs the receiver operating characteristic (ROC) curve 430, one can see that the EEG feature alone predicts with accuracy approximately 65% of the time as defined by the summary ROC Area Under the Curve (AUC) statistic.

Figure 19:
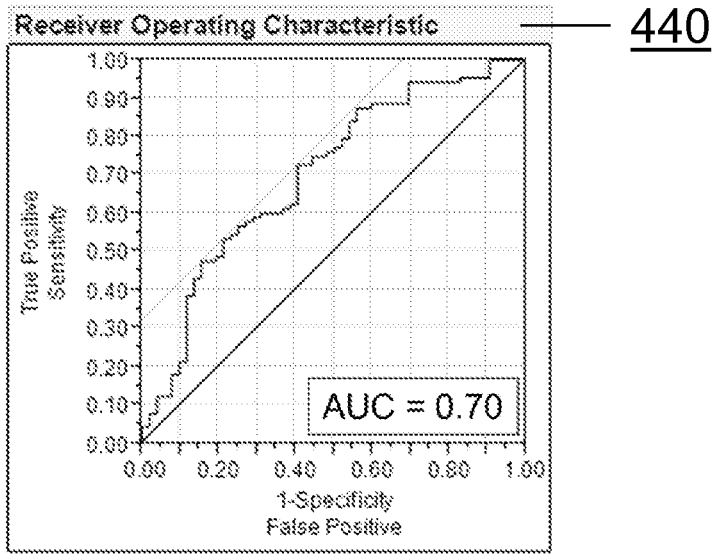
FIG. 19 is a pair of graphical displays of the Receiver Operating Characteristic curve (ROC) of an EEG feature (relative beta) combined with a cognitive task score from the King-Devick test as a pair (upper plot) or in combination with two co-variates, age and gender (lower plot), a multi-modal predictive model consistent with the present invention. The Area Under the Curve (AUC) is shown as well.
Figure 19:
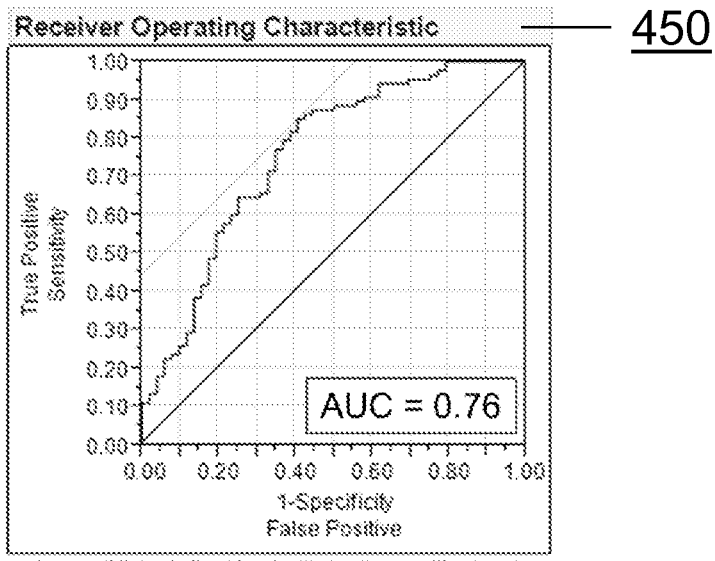

FIG. 19 illustrates in ROC plot 440 that the area under the curve (AUC) is now 70% when the King-Devick final test time in seconds (a cognitive measure of the subjects brain) is combined with the relative beta EEG power (a brainwave measure), creating a multi-modal signature. When one adds the co-variates of age and gender, the AUC raises to 76% as shown in ROC plot 450, fully corroborating the system and methods of the invention. As one adds additional modalities of information, from either the accelerometers, the microphone from voice analysis, from the camera for image analysis or eye tracking, one can anticipate that the accuracy of the predictive model will increase further as it aids healthcare providers in the diagnosis of a given condition. This exemplifies the power of a multi-modal system of objective biosensors to assess brain health and function.

Use of Correlation Analysis Across Time Series in the Multi-Modal Bio Signal Data Streams The present invention explicitly contemplates the use of two point, three point or higher order correlations in time to examine interactions between the various bio-sensor data streams. For instance, one could look at the time series of samples from a microphone sampled at 8 KHz and the EEG from a single lead sensor sampled at 512 Hz and look at any of the various two point correlation functions available in the literature or MATLAB tool boxes. Note that one can play with both spatial variables as biosensors can be spatially in different locations or temporally where the variable data streams are occurring either in real-time simultaneously or with a defined or calculated lag in time between variables of interest (so called phase shift by some). In addition, techniques such as spatial coherence and concordance can be used either between two sensors of the same modality (which is typically done for EEG) but similar approaches can be adapted to the multiple but different modality streams of bio signal data from the system of the present invention.

As CPU processing power increases into smaller form factors, one can envision the real-time processing of multiple biological signal data streams through embedded digital signal processors (DSPs) and other high end MCU devices embedded within the head REM or trunk located REM or extremity located REM modules.

Use of an Infra-Red Eye Tracker During Neuro-Opthalmologic Tasks

As an alternate approach to a Google Glass eye tracker, one could employ other dedicated hardware such as from Tobii, GazePoint or other eye tracker manufactures which stream left and right eye position and pupil diameter measurements continuously. From the output eye gaze position, one can make measurements of fixation on various objects in a stimuli field of view, as well as saccades or anti-saccades which are of interest. Stimulation visuals could include instructions, static photographs or artistic creations, movies, web pages, advertisements, pdf documents, etc. Predefined areas of interest (AOI) can be created and the eye gaze data superimposed on top of the areas of interest to define metrics of fixation and saccade relative to the AOI's. Candidate metrics can be extracted from the eye gaze data to include time to first fixation, fixation duration, total fixation duration, visit duration, total visit duration, percentage fixated, saccade accuracy, anti-saccade accuracy to name some non-limiting examples of features extracted from the raw eye gaze data streams. These extracted features can then be incorporated into summary feature tables of the present invention and used to construct multi-variate signatures and classifiers along the with extracted brainwave features, speech recognition features, neuropsychological test data, accelerometer based balance measures, etc.

EXAMPLES

While the above description contains many specifics, these specifics should not be construed as limitations on the scope of the invention, but merely as exemplifications of the disclosed embodiments. Those skilled in the art will envision many other possible variations that are within the scope of the invention. The following examples will be helpful to enable one skilled in the art to make, use, and practice the invention.

Example 1

TIRHR Concussion Study

In collaboration with an non-profit mountain based medical institute near Lake Tahoe, two groups of subjects were enrolled in an Institutional Review Board approved clinical protocol, wherein the first group of subjects (group A) were clinically diagnosed with a concussion (mTBI) or mild traumatic brain injury and second control cohort of subjects (group B) were enrolled who did not have any issue with concussion and served as Controls (CTL) were recruited under the supervision of an Institutional Review Board. Participants from both groups A and B were scanned identically with an electronic REM module including a single electrode EEG device as described in PCT Patent Application PCT/US2012/046723, filed Jul. 13, 2012. The 5 minute scan protocol included 30 seconds Eyes Closed, 30 seconds Eyes Open, approximately 3 minutes to conduct the King-Devick test and then closed with a 30 seconds Eyes Closed, 30 seconds Eyes Open block again. The stop watch times and errors for each card of the King-Devick test were recorded manually by the test administrators while the peripheral MCU (a laptop computer) presented the cards and recorded the responses of the individuals via the microphone. The head based REM module continuously recorded the forehead EEG from position Fp1 relative to mastoid on the ear for reference REF and ground GND. The data was encrypted locally before being transported over a secure pipe to a virtual server in cyberspace.

Signal analysis scientists were blinded to participant clinical diagnosis for the purposes of artifact detection, signal processing and feature extraction. The extracted feature data table was then quality controlled and scrubbed to remove as many errors as possible. The total time for the King-Devick test was calculated according to the published procedure of using the minimal number of errors and then summing the individual times to read all three cards in succession. This total time represents one extracted variable and underwent a logistic classification model. The result of this model indicated that the King-Devick total time in seconds alone predicted the classification of the individuals approximately 62% of the time (AUC=0.62).

Independently, analysis for the parallel data stream of EEG brainwave information, sampled at 128 samples per second with 10-bits of amplitude resolution was then Fourier transformed to determine the spectral properties. The relative power in each of the delta, theta, alpha, beta and gamma bands was analyzed in a logistic classification model where the EEG feature was the predictor x-variable and the clinical outcome (grp A or B) was the outcome y-variable in the model. The analysis was conducted in JMP Pro v10 from SAS (Cary, N.C.).

In FIG. 18, one can see the logistic plot 420 for the relative-beta power (from 12-30 Hz) showing a decreased relative beta power in the concussed group A relative to control group B. When one constructs the receiver operating characteristic (ROC) curve 430, one can see that the EEG feature alone predicts with accuracy approximately 65% of the time as defined by the summary AUC statistic. In FIG. 19, one can see in ROC plot 440 that the area under the curve (AUC) is now 70% when the King-Devick test time (a cognitive measure of the subjects brain) is combined with the relative beta EEG power (a brainwave measure), creating a multi-modal signature. When one adds the co-variates of age and gender, the AUC raises to 76% as shown in ROC plot 450, fully corroborating the system and methods of the invention. As one adds additional modalities of information, from either the accelerometers, the microphone from voice analysis, from the camera for image analysis, one can anticipate that the accuracy of the predictive model will increase further as it aids healthcare providers in the diagnosis of a given condition. This exemplifies the power of a multi-modal system to assess brain health and function.

Example 2

Lehigh University Sports Medicine Concussion Study

In collaboration with an NCAA Division 1 university, several groups of subjects were enrolled in an Institutional Review Board approved clinical protocol, wherein the first group of subjects (group A) were clinically diagnosed with a concussion (mTBI) or mild traumatic brain injury, a second control cohort of subjects (group B) were enrolled who did not have any issue with concussion and served as non-injured Control ssubjects (CTL), while other athletes from other sports (Group C, etc.) were recruited under the supervision of an Institutional Review Board as well. Participants from groups A, B, C and others were scanned identically with an electronic REM module including a single electrode EEG device as described in PCT Patent Application No. PCT/US2012/046723, filed Jul. 13, 2012. The 22-24 minute scan protocol included 1 minute of Eyes Closed, 1 minute of Eyes Open, an automated application of the Graded Symptom Checklist from the SCAT-2, elements of the Standard Assessment of Concussion (SAC) including orientation, immediate memory recall, concentration, delay memory recall, a full Balance Error Scoring System (on both firm and foam surfaces), King-Devick Test Cards, binaural beat audio stimulation at 6 and 12 hertz beat frequency centered at 400 Hz, photic stimulation, and a fixation task including a moving red cross for 1 minute.

The stop watch times and errors for each card of the King-Devick test were recorded manually by the test administrators while the peripheral MCU (a Dell Vostro 3550 laptop computer) presented the cards and recorded the responses of the individuals via the microphone and mouse clicks. The BESS errors were recorded manually as well as the SAC responses. The head based REM module continuously recorded the forehead EEG from 10-20 montage position Fp1 relative to mastoid on the ear for reference REF and ground GND. A multi-modal assessment consisting of an EEG data stream, a cognitive data stream (reaction time and accuracy), self-report of concussion symptoms, and a microphone data stream were recorded depending upon which tasks were being conducted. The data was encrypted locally before being transported over a secure connection pipe to a secure virtual server in cyberspace.

Signal analysis scientists were blinded to participant clinical diagnosis for the purposes of artifact detection, signal processing and feature extraction. The extracted feature data table was then quality controlled and scrubbed to remove as many errors as possible. The total time for the King-Devick test was calculated according to the published procedure of using the minimal number of errors and then summing the individual times to read all three cards in succession. This total time represents one extracted variable and underwent a logistic classification model. Serial assessments were conducted on both concussed athletes and controls with from three to up to ten scans assessing both concussed and controls.

Figure 20:
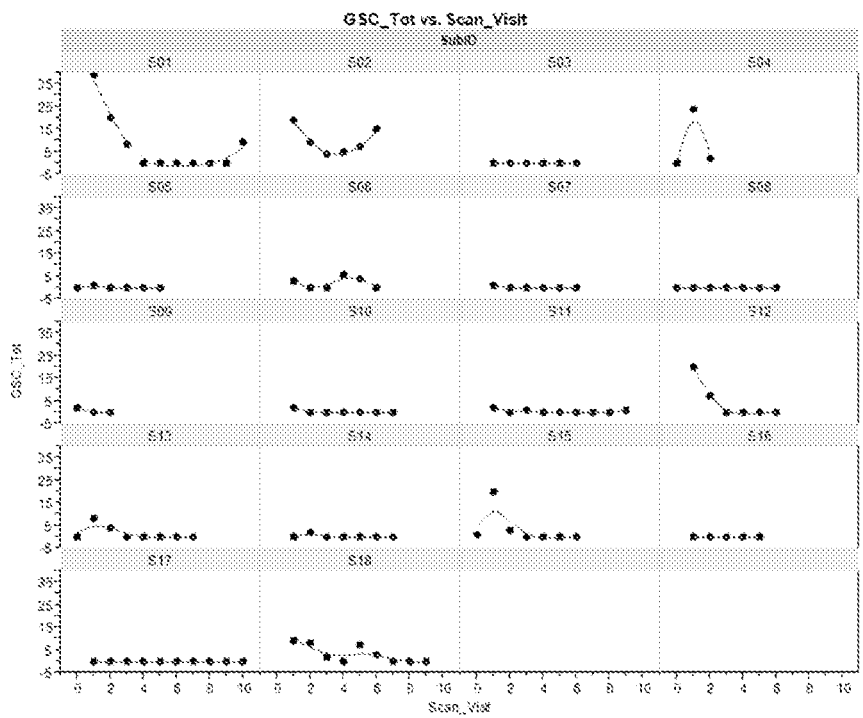
FIG. 20 is a graphical representation of the Graded Symptom Checklist total score (along the y-axis) upon serial assessment at several different scans noted along the x-axis as scan visit for N=18 eighteen subjects. Flat trajectories appear free from symptoms while several subjects appear to exhibit symptoms consistent with concussion.
Figure 21:
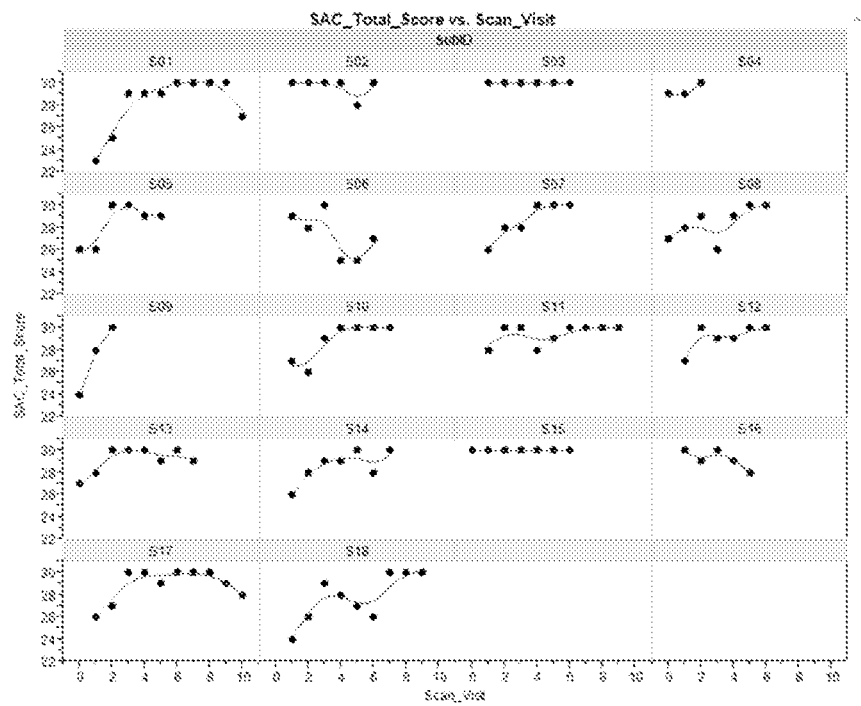
FIG. 21 is a graphical representation of the Standard Assessment of Concussion (SAC) total score (along the y-axis) upon serial assessment at several different scans noted along the x-axis as scan visit for N=18 eighteen subjects. Flat trajectories appear near 30 (a perfect score)

As can be seen in FIG. 20 and FIG. 41 for the total scores of the Graded Symptom Checklist, some subjects appear flat or normal in their symptoms, while others (such as subject S16 in FIG. 20) show dramatically elevated levels of symptoms consistent with concussion, which resolve in time back to no symptoms. FIG. 21 and FIG. 42 shows the total score from the Standard Assessment of Concussion (SAC) with a maximum healthy value of 30 points plotted along the y-axis across time measured in several different scan visits along the x-axis. Flat trajectories which appear near 30 (a perfect score) appear cognitively intact (such as subject S03 of FIG. 20) while several subjects (such as subject S07 of FIG. 20) appear to exhibit cognitive issues consistent with concussion which resolve in later scan visits. In FIG. 22 and FIG. 43, the Balance Error Scoring System (BESS) total error score (summed across all three stances on both a firm and foam surface) is plotted in time across scan visits (which are not necessarily at equal intervals of time between them in days. One can see that flat trajectories which are observed near zero (a perfect score) appear relatively stable within their vestibular system while several subjects appear to exhibit balance and vestibular issues consistent with concussion, shown as an elevated number of errors which decline with meaningful slope over time till they plateau within some fluctuations around normal performance.

The final slice of this data can be seen in FIG. 23 and FIG. 44, where the King-Devick Ophthalmologic Test (Oride et al 1986) total time, summed across three test cards in seconds is plotted vertically across scan visit on the longitudinal or x-axis. Flat trajectories that hover around a minimum value (typically forty seconds) appear consistent and stable in their neuro-ophthalmological processing, a typically represent healthy non-injured controls subjects, while several subjects (such as S01 and S12 in FIG. 23) appear to take longer times at early scan visits which then relax down to a stable and consistent amount of time, consistent with a concussion phenotype where the brain injury resolves itself over days to weeks and a baseline level of performance re-emerges. FIG. 45 provides a pair-wise view of the same data in FIG. 44 where the concussed subject and their non-injured teammate control comparator subject are plotted together.

It should be clear from the previous four sets of data in FIG. 20 thru FIG. 23 and FIG. 41 thru FIG. 44, that one can combine a symptom data stream, a cognition data stream, a balance/vestibular data stream and a neuro-ophthalmologic data stream into a multi-variate composite consistent with the present invention. Moreover, cross correlation and predictive models can be built from this and other bio signal data streams including the EEG data stream and the microphone data stream, not yet included in the analysis shown.

Further analysis by pairing the concussed and non-injured control subjects together can reveal interesting information as shown in FIG. 24 through FIG. 27, which are the same four metrics just plotted pairwise on the plot for both the concussed athlete and their non-injured comparator teammate control. Interestingly, FIG. 28 shows the relative beta power in 9 pairs of athletes, with the concussed athlete in red and the non-injured teammate control in green. The results appear mixed as some subjects exhibit the literature reported lowering of relative beta in TBI (such as the A pair or the E pair or the G pair). Moreover, analysis of baseline adjusted first scans after a "putative event" can help aid in the assessment of a putative concussion in a human subject as shown in FIG. 29 through FIG. 33.

For instance in FIG. 29, in seems clear in the limited sample that the elevated GSC above 5 at visit 1 is distinct for concussed subjects and not for controls. Thus, the very limited data supports a predictive biomarker of $GSC_{total}$ (Visit1)−$GSC_{total}$ (baseline=visit0)>5 as "likely concussed." However, upon review of the additional data from FIG. 41, one can conduct an item analysis of each question within the GSC and learn that the top most important elements or questions within the GSC (from most important to least important) are 1) "Do you have a Headache", 2) the total or GSC-Sum, 3) "Don't Feel right", 4) "slowed down", 5) "In a Fog", 6) "Pressure in the head", 7) "Dizzy", 8) "Difficulty Concentrating", 9) "Fatigue", 10) "Drowsy", 11) "Sensitivity to Light". Thus if one wanted to shorten the GSC in time and pair down the number of questions but not reduce the discriminatory power, one could construct a shortened "GSC-short" consisting of the top 8, 9, 10 or 11 items from the 18 element GSC.

From FIG. 30, the concussed athletes are not showing a distinct change from baseline for the standard assessment of concussion in its totality. However if one analyzes the individual components of the SAC, one sees that the most important SAC elements include (from most to least important) the Delayed Memory, Concentration, SAC-total score, Immediate memory, Orientation. Thus, if one wanted to shorten the SAC while maintaining diagnostic discriminatory power, one could include in a shortened SAC only the Delayed memory and Immediate memory elements of the SAC, or alternatively include the Concentration component as well. The Orientation element does not appear to confer much discriminatory power.

From FIG. 31, it appears that the BESS total error score is a variable that does not appear to be reliable in such a small sample of human subjects. Additional data is now available from that shown in FIG. 43, which supports the earlier perspective. On the other hand, if one investigates each of the six elements of the BESS (from most to least important), one fines that the elements sort as: BESS-TandemStance-FirmSurface, BESS-TandemStance-FoamSurface, BESS-TotalErrors, BESS-SingleFoot-FoamSurface, BESS-SingleFoot-FirmSurface, BESS-DoubleStance-FoamSurface, and lastly BESS-DoubleStance-FirmSurface. Thus, if one uses just the foam, it reduces the task by 50% yet appears it will remain helpful.

From FIG. 32, the total time for the K-D task appears quite variable as well with limited data; however, if one includes the results from FIG. 44, it appears clear that saccade based card tasks are an important means to differentiate.

Moreover, in FIG. 34, a montage of four non-injured control subjects can reveal interesting patterns in the five modes of data presented graphically. In FIG. 35, a montage of four mTBI injured subjects can reveal interesting patterns in the five modes of data presented graphically. Lastly, a direct comparison of one non-injured athlete to the injured (mTBI) athlete can provide observational signatures that can differentiate different groups of individuals. In FIG. 36, the GSC, SAC, BESS, KD time, and relative beta power (along the y-axis, respectively from top to bottom) are each individually stacked on top of each other for each scan visit (along the x-axis), which is useful in Return-To-Learn, Return-To-Play, Return-to-Work, Return-to-Duty, and Return-to-Activity decision making.

Example 3

Rothman Concussion Study

In collaboration with a clinical practice and a concussion expert, two groups of subjects were enrolled in an Institutional Review Board approved clinical protocol, wherein the first group of subjects (group A) were clinically diagnosed with a concussion (mTBI) or mild traumatic brain injury and a second control cohort of subjects (group B) were enrolled who did not have any issue with concussion and served as Controls (CTL) and were recruited under the supervision of an Institutional Review Board. Participants from both groups A and B were scanned identically with an electronic REM module including a single electrode EEG device as described in PCT Patent Application No. PCT/US2012/046723, filed Jul. 13, 2012. The 25 minute scan protocol included 1 minute Eyes Closed, 1 minute Eyes Open, and then approximately 25 minutes of scanning while the student athlete completed the ImPACT computer test with a head electronic REM module streaming EEG data to a nearby peripheral MCU (Dell Vostro 3550 laptop). Key clicks on the peripheral MCU laptop indicated the temporal beginning and ending of each of the various tasks within the ImPACT computer assessment. This represents another multi-modal assessment combining neuropsychological testing, EEG, and clinical observation in accordance with the invention.

Example 4

Google Glass Implementation of *Borealis* Software

In collaboration with BrickSimple LLC, we implemented our Android application software *Borealis* to run as glassware in the Google Glass, this enables access to various bio-sensors such as the built in 3-axis Invensense accelerometer with 3-axis gyrometry, and 3 axis electronic-compass. This combination of biosensors enables software running on the Glass to make medical and wellness measurements and report them in a responsible fashion. We successfully deployed our app from an Android tablet to the Glass based "Glassware" and incorporated the accelerometer and eye blink detection. Furthermore, Glassware based software has been successfully deployed to the android device and automated pairing and initiation of the software in a Glass consistent user interface.

Example 5

Tobii X2-30 Compact Eye Tracker Implementation

We successfully incorporated a Tobii X2-30 Compact eye tracker into our data acquisition paradigm. FIG. 37 shows a schematic of a laptop PC 500 screen but it could equally work for a tablet or smartphone form factor. The eye tracker 510 is plugged into a USB port 520 in the present wired mode, but Wi-Fi or other wireless connectivity is contemplated as well. First, stimuli were created to check the analytical performance of the eye tracker to extreme conditions. Numbers were placed on slides in the corners of the screen and shown for 2 second intervals before moving onto the next corner in a clockwise rotation. Eye position was plotted for both eyes averaged as shown in FIG. 38. The output of the eye tracker very nicely produced the expected trace with the 16:9 aspect ratio apparent in the asymmetric x position and y position.

In a follow-up experiment, neuro ophthalmologic saccade cards (King Devick test) were presented while recording EEG brainwaves, the microphone and the forward facing webcam on a laptop. FIG. 39 shows a heat map representation of where the eye gaze was concentrated in time relative to the stimulation numbers on the various cards. Thus it is quite clear that while the brain reads off a number from the car, a fixation in time occurs while the eye stares at one point in space rather than moving from fixation to fixation as a saccade. FIG. 40 shows the use of various predefined Areas of Interest (represented as circles centered on the numbers on the card) to enable extractable biomarker measurements of eye gaze that intersect with the AOIs to define time durations, fixations, and saccade accuracy as the subject attempts to track the targets of interest. One can see in FIG. 40 the appearance of significant eye gaze taking place "off target" at the beginning of a given row relative to the end of the same row. Thus, one can clearly see that the percent accuracy for the first number on the left of a row is an excellent biomarker as is the percent of time outside the first number. Less useful would be those extracted features from the right hand most numbers at the end of a given row on the cards.

Those skilled in the art will also appreciate that the invention may be applied to other applications and may be modified without departing from the scope of the invention. For example, the signal processing described herein may be performed on a server, in the cloud, in the electronics module, or on a local PC, tablet PC, smartphone, or custom hand held device. Accordingly, the scope of the invention is not intended to be limited to the exemplary embodiments described above, but only by the appended claims.

What is claimed:
1. A system for capturing multiple streams of biological sensor data for assessing brain health of a user, comprising:
    an electronics module including an active brainwave sensor that is adapted to collect from a user's head at least one channel of electroencephalography (EEG) brainwave data;
    a processor;
    a plurality of biological sensors co-registered in time to simultaneously record biological sensor data from the user, said biological sensors including at least three of the following: a microphone that records human speech to capture verbal responses of the human subject during one or more tasks; an image sensor that records eye position, eye saccade and other biometric identification information; an accelerometer; a gyrometer; a thermometer; a pulse oximetry sensor; a dermal skin conductance sensor; and
    one or more stimulation devices that apply one or more tasks including one or more of a visual or photic stimulant to the user, an auditory stimulant to the user, a gastronomic stimulant to the user, an olfactory stimulant to the user, a touch stimulant to the user, and a cognitive challenge stimulant to assess brain function of the user,
    wherein the plurality of co-registered biological sensors simultaneously measure the body's response to stimulants applied by said one or more stimulation devices and the processor processes outputs of the plurality of co-registered biological sensors in response to the stimulants to assess the user's brain health.
2. The system of claim 1, further comprising a peripheral microprocessor control unit (MCU) in the form of a laptop computer, tablet computer or smartphone like device that simultaneously captures biological signal streams collected by said plurality of biological sensors.
3. The system of claim 1, further comprising at least one peripheral electronics module that is positioned on the trunk or limbs of the user to collect position and heart rate data that is co-registered in time with data collected by said electron- ics module so that the collected biological sensor data can be analyzed either alone in isolation or in a cross-correlative fashion.

4. The system of claim 1, wherein the electronics module further comprises light emitting diodes for photic stimulation.

5. The system of claim 1, further comprising a peripheral device that displays images or movies to the user to stimulate the visual system while the biological sensors collect the user's brain response to the stimulation.

6. The system of claim 1, wherein the electronics module includes electrodes equally divided into 2, 3 or 4 equivalent but independent electrodes.

7. The system of claim 1, wherein the electronics module includes a mass storage device for storage of collected biological sensor data.

8. The system of claim 1, wherein the one or more stimulation devices apply stimuli to at least one of the user's senses and the electronics module collects biological sensor data from biological sensors that collect biological sensor data indicative of a response from another of the user's senses.

9. The system of claim 8, wherein the one or more stimulation devices present photographic images to the user while the electronics module collects at least one of skin conductance measurements, brainwave EEG, eye position, and accelerometer measurements while the photographic images are presented.

10. The system of claim 1, wherein the one or more tasks include symptom questions.

11. The system of claim 1, wherein the one or more tasks include Immediate and Delayed Memory tasks of a Standard Assessment of Concussion.

12. The system of claim 11, wherein the one or more tasks further include a Concentration Task of the Standard Assessment of Concussion.

13. The system of claim 1, wherein the one or more tasks include only three foam or unstable pillow based postures of the Balance Error Scoring System (BESS) total error score.

* * * * *